(12) United States Patent
Berkvens-Matthijsse

(10) Patent No.: US 10,666,444 B2
(45) Date of Patent: May 26, 2020

(54) CONTROLLED, SECURE EXCHANGE OF PRIVACY SENSITIVE DATA UNITS

(71) Applicant: ZD Exploitatie B.V., Nijmegen (NL)

(72) Inventor: Sven Berkvens-Matthijsse, Haler (NL)

(73) Assignee: Consumer Health Entrepreneurs B.V., Nijmegen (NL)

( * ) Notice: Subject to any disclaimer, the term of this patent is extended or adjusted under 35 U.S.C. 154(b) by 175 days.

(21) Appl. No.: 15/775,539

(22) PCT Filed: Nov. 11, 2016

(86) PCT No.: PCT/NL2016/050787
§ 371 (c)(1),
(2) Date: May 11, 2018

(87) PCT Pub. No.: WO2017/082731
PCT Pub. Date: May 18, 2017

(65) Prior Publication Data
US 2018/0359098 A1   Dec. 13, 2018

(30) Foreign Application Priority Data

Nov. 11, 2015   (NL) .................................. 2015772

(51) Int. Cl.
*G06F 21/60* (2013.01)
*H04L 9/32* (2006.01)
(Continued)

(52) U.S. Cl.
CPC ........ *H04L 9/3247* (2013.01); *G06F 21/6245* (2013.01); *G16H 10/60* (2018.01);
(Continued)

(58) Field of Classification Search
CPC ............... H04L 9/3247; H04L 63/0823; G06F 21/6245
See application file for complete search history.

(56) References Cited

U.S. PATENT DOCUMENTS

| | | | |
|---|---|---|---|
| 7,587,368 B2 * | 9/2009 | Felsher ................. | G06F 19/328 705/65 |
| 8,904,181 B1 * | 12/2014 | Felsher ................. | H04L 9/0825 380/282 |

(Continued)

FOREIGN PATENT DOCUMENTS

EP   2882156 A1   6/2015

OTHER PUBLICATIONS

Jing Jin et al., "Patient-Centric Authorization Framework for Sharing Electronic Health Records," SACMAT'09 (Jun. 3-5, 2009), Stresa, Italy, Copyright 2009 ACM 978-1-60558-537—Jun. 9, 2006, pp. 125-134.

(Continued)

*Primary Examiner* — Wasika Nipa
(74) *Attorney, Agent, or Firm* — Leydig, Voit & Mayer, Ltd.

(57) ABSTRACT

A method is provided for controlling exchange of privacy sensitive data between a first certified party server (A) associated with a first party and at least a second certified party server (B) associated with a second party using a certified intermediate server (Y) subject to authorizations ($X_{AB}$) imposed by an authorizing party (X), using a public network. Therein the first certified party server (A) transmits (S2) to the certified intermediate server (Y) a primary request ($ARQ(I_{xA}, \Gamma_{xA})$) that includes a digitally signed primary request indication ($I_{xA}, \Gamma_{xA}$) comprising a primary request indication ($I_{xA}$) specifying a set of privacy sensitive data units ($X_A$) for which a copy ($C_{xA}$) is requested and a digital signature ($\Gamma_{xA}$) of said first party, associated with said primary request indication ($I_{xA}$). The certified intermediate server (Y) determines (S3) which authorizations are provided by the authorizing party (X) for transmission of information concerning privacy sensitive data from the (Continued)

second certified second party server (B) to the first certified party server (A). The certified intermediate server (Y) executes (S4) a query procedure (QP) in which at least includes transmitting the digitally signed primary request ($I_{XA}, \Gamma_{XA}$) by the certified intermediate server (Y) to the second certified party server (B). The second certified party server (B) inspects (S5) the digital signature ($\Gamma_{XA}$) to verify authenticity of said the primary request. Subject to confirmation of its authenticity it makes available a provider copy ($C_{XAMB}$) including at least a censored copy, being a copy of a censored subset of privacy sensitive data units, the censored subset comprising the privacy sensitive data units as specified by the primary request indication ($I_{XA}$) subject at least to said authorizations ($X_{AB}$) and subject to availability thereof with the at least a second certified party server. It also provides a second party digital signature, i.e. a digital signature ($\Gamma_B$) of the second certified party, associated with the censored subset. Upon completion of the query procedure, the censored copy and the second party digital signature are made available to the first certified party server as a digitally signed authorized copy.

37 Claims, 11 Drawing Sheets

(51) Int. Cl.
  *H04L 29/06* (2006.01)
  *G16H 10/60* (2018.01)
  *G06F 21/62* (2013.01)
(52) U.S. Cl.
  CPC .......... *H04L 9/321* (2013.01); *H04L 63/0823* (2013.01); *H04L 2209/88* (2013.01)

(56) References Cited

U.S. PATENT DOCUMENTS

2002/0194131 A1\* 12/2002 Dick ................. G16H 10/60
  705/51
2011/0099376 A1\* 4/2011 Gupta .................... H04L 9/321
  713/171
2014/0331297 A1 11/2014 Innes et al.

OTHER PUBLICATIONS

European Patent Office, International Search Report in corresponding International Application No. PCT/NL2016/050787 dated Mar. 1, 2017 (3 pages).

\* cited by examiner

CONTROLLED, SECURE EXCHANGE OF PRIVACY SENSITIVE DATA UNITS

CROSS-REFERENCE TO RELATED APPLICATIONS

This patent application is a U.S. National Phase of PCT International Application No. PCT/NL2016/050787, filed Nov. 11, 2016, which claims priority to Netherlands Application No. 2015772, filed Nov. 11, 2015, which are both expressly incorporated by reference in their entireties, including any references contained therein.

BACKGROUND OF THE INVENTION

The present invention relates to a method for controllably and securely exchanging privacy sensitive data units.

The present invention further relates to a system for controllably and securely exchanging privacy sensitive data units.

The present invention still further relates to a certified intermediary server for controllably managing a secure exchange of privacy sensitive data units between certified party servers.

The present invention still further relates to a certified party server for controllably sharing privacy sensitive data units with other certified party servers in a secure manner.

Privacy sensitive data, e.g. medical data concerning a patient, may be distributed between different institutions. For example one institution may be the patient's general practitioner holding records about previous consults by the patient, another institution is a diagnostic center which stores medical imaging data and again another institution is a hospital associated with a medical specialist treating the patient. On the one hand it is desired to provide for an efficient exchange of medical data, for example enabling the medical specialist to obtain all necessary information to optimally treat the patient. On the other hand such exchange should be carefully controlled to ensure that the exchanged privacy sensitive data is visible only to authorized parties. In particular, new legislation demands explicit and specific approval by the person involved, e.g. the patient to which the medical data relate. The person involved may assign for each data unit a different authorization, therewith providing a set of authorizations defining for each combination of a requesting party and a potentially providing party, which privacy sensitive data may be transmitted by that potentially providing party to the requesting party and which requests may be received by the potentially providing party from the requesting party. This may for example depend on the degree of confidentiality guaranteed by an institution. The person involved may for example specify that an institution having a lower degree of confidentiality does not receive certain privacy sensitive data units, e.g. psychiatric records, whereas the same person authorizes that institution to provide information about his blood type. The authorization given by the person involved may for example depend further on the reliability of the data provided by an institution. The person may for example exclusively authorize a particular institution to provide X-ray imaging data, as this particular institution is known to provide this data at a high quality. Although in some instances private networks may be available for the exchange, in practice a public network is available. As indicated above, the set of authorizations may also include authorizations specifying which requests may be received by the potentially providing party from the requesting party.

This is because a request for privacy sensitive data concerning a person can be indicative about that person's situation or mental or physical state. For example a request to provide a copy of a psychiatric report of a persons implies or suggests the existence of a psychiatric disorder. In addition, even the set of authorizations itself is to be treated as privacy sensitive as such authorizations or the lack thereof are indicative of a person's situation or mental or physical state, for example an indication in said set of authorizations that certain institutions are not authorized to receive requests or responses concerning HIV medication. Accordingly, there is a need to provide means that enables authorized control of exchange of privacy sensitive data between certified parties on a public network while avoiding intrusion by unauthorized parties and while restricting access to said authorizations by other parties, including said certified parties.

SUMMARY OF THE INVENTION

According to a first aspect of the invention a method is provided as claimed in claim 1.

According to a second aspect of the invention a system is provided as claimed in claim 23.

According to a third aspect of the invention a certified intermediary server is provided.

According to a fourth aspect of the invention a certified party server is provided.

Aspects of the present invention enable a reliable exchange of privacy sensitive data between certified party servers via an authorization controlled intermediary server using a public network such as the Internet. Therein, the certified party server requesting privacy sensitive data and the certified party server providing privacy sensitive data can verify authenticity of each others responses, even if they do not directly communicate with each other. As part of the intermediated interaction between the first certified party server and the at least a second certified party server, the at least a second certified party server receives the digitally signed request from the first certified party server. This enables the second certified party server to assure that it responds to an authentic request, while the certified intermediary server can provide additional indications that specify to what extent the second certified party server can respond to this request. Likewise, the first certified party server can assure that it receives a true response from the second certified party server, while enabling moderation by the certified intermediary server in accordance with the authorizations provided by the authorizing party. As the certified intermediary server is provided (in addition to the first and second certified party servers) to perform this task, it is further possible to restrict knowledge of said certified party servers about these authorizations. According to the present invention a certified first party server may request the certified intermediary server to execute a query procedure with one or more second certified party servers, so as to obtain a digitally signed authorized copy of privacy sensitive data from the one or more second certified party servers. The certified first party server may issue the request to the certified intermediary server for example by sending a message, including the request. Alternatively, the certified intermediary server may poll known certified party servers to determine if they have a pending request. Data may be made available by a server to another server by transmitting a message, but alternatively, a server may make data available by enabling the other server to download the data.

In the sequel the wording "making available to" is used to specify that the target has direct access to the data made available. The wording "making available for" is used to specify that the target is the intended recipient of the data, but that it may receive the data via another server, possibly subject to further certain requirements.

Data can be made available to a target for example by transmitting the data in a message or by allowing the target to download the data from a source.

Embodiments may be contemplated wherein the at least a second certified party server makes available its digitally signed authorized copy directly to the requesting first certified party server, for example by transmitting a response with the digitally signed authorized copy to the first certified party server. Preferably however, the at least a second certified party makes available its digitally signed authorized copy always via the certified intermediary server. I.e. the at least a second certified party server makes available the digitally signed authorized copy to the certified intermediary server, and the certified intermediary server subsequently makes available the digitally signed authorized copy to the first certified party server. In this way it is possible to verify that the provider response indeed complies with the authorizations provided by the authorizing party. Therewith a fail safe protection can be provided for the inadvertent case that the at least a second certified party server is not operating properly, e.g. by malware installed thereon.

Embodiments are further contemplated wherein the at least second certified party server provides the constituents of the digitally signed authorized copy separately, for example by first providing a copy that includes at least a copy of a censored subset of privacy sensitive data units and to provide its digital signature associated with the censored subset before or after providing said copy. I.e. a "censored subset" is used to denote the privacy sensitive data units as specified by the primary request indication ($I_{XA}$) subject at least to said authorizations ($X_{AB}$) and subject to availability thereof with the at least a second certified party server. It is noted that the copy provided by the at least a second certified party server may include copies of additional privacy sensitive data, e.g. it may include all privacy sensitive data indicated in the primary request, or all privacy sensitive data for an authorizing party. However, in any case the certified intermediary server it is prevented that the first certified party server receives copies of privacy sensitive data for which the authorizing party has given no authorization to provide these to the first certified party server at all or has given no authorization to the at least a second certified party server to provide these to the first certified party server directly or indirectly. Accordingly, in configurations wherein the at least a second certified party server provides the copy of the censored subset as part of a copy that may further include data for which no authorization is given, it should provide that copy including the copy of the censored subset always to the certified intermediary server. The certified intermediary server may then verify whether or not the copy includes such data for which no authorization is given. If it determines a lack of authorization it may select the copy of the censored subset from the copy it received from the at least a second certified party server and subsequently make that selection available to the first certified party server. Alternatively, it may request the at least a second certified party server to provide only a copy of the censored subset. If it determines that the copy it received from the at least a second certified party server complies with the given authorizations, it can forward the copy to the first certified party server.

The at least a second certified party server may make available its digital signature associated with the censored subset directly to the first certified party server or alternatively make it available indirectly to the first certified party server via the certified intermediary server. Combinations are possible, wherein the at least a second certified party server makes available the copy of the censored subset directly to the first certified party server, and makes available its digital signature either directly or indirectly to the first certified party server. Likewise, combinations are possible, wherein the at least a second certified party server makes available the copy of the censored subset indirectly to the first certified party server, and makes available its digital signature either directly or indirectly to the first certified party server. The only restriction therein is that the certified intermediary server assures that all data transfers comply with the authorizations given by the authorizing party. Preferably however, both the copy of the censored subset and the digital signature of the second certified party associated therewith are provided to the first certified party server indirectly, i.e. via the certified intermediary server. This enables an optimal control of the exchange of privacy sensitive data and also provides opportunities to configure the certified intermediary server as a single interface to the first certified party server also if the certified intermediary server executes the query procedure with a plurality of second certified party servers that could potentially provide the requested data.

In an embodiment, the at least a second certified party server also provides a provider response in case the subset of privacy sensitive data for which it is authorized to provide a copy to said first certified party server and which it has available is an empty set. In this case the provider response comprises as the digitally signed authorized copy an indication indicating that said subset is empty and a digital signature of said at least a second party, associated with said indication. This implies that the at least a second certified party server issues a provider response whether or not that response actually contains copied privacy sensitive data. This is advantageous, in that an external party cannot easily determine whether or not the at least a second certified party server has actually delivered copied privacy sensitive data. In addition, when a first certified party server A does not receive copied privacy sensitive data which it requested, this does not reveal to A whether this is because server B is not allowed to send these data, or server B does not have that privacy sensitive data, or because of both these reasons.

In the sequel the wording subset is used to indicate a set of privacy sensitive data units that includes a part, none or all of the privacy sensitive data units. I.e. this includes a set which is identical to another set.

As indicated above, configurations exist, wherein the second certified party server has the authorization information that indicates for which privacy sensitive data units it is authorized to provide a copy to the first certified party server that issued the primary request that initiated the query procedure. Provided further that the second certified party server is configured and capable to provide the copied privacy sensitive data units in accordance with that authorization information, i.e. to provide a censored copy, it can either make available the copied privacy sensitive data units directly to the first certified party server that issued the primary request, or it can make available the copied privacy sensitive data units to the first certified party server via the intermediary certified party server. Also a further approach is considered wherein the second certified party server is configured to selectively make available a first portion of the censored copy directly to the first certified party server and a second portion of the censored copy to the first certified party server via the certified intermediary server. For example, the default selection may be to make available all copy privacy sensitive data to the first certified party server via the certified intermediary server. However, the second certified party server may have a policy to deviate from this default approach for certain categories of privacy sensitive data. In that case it may either not make available copies of this privacy sensitive data, and only make available copies of the remainder of the requested privacy sensitive data. However, it may also make available copies of privacy sensitive data belonging to this categories directly to the first certified party server, whereas it makes available the copies of the remainder privacy sensitive data units to the first certified party server via the certified intermediary server. In this way it can hide the privacy sensitive data units in these categories before the intermediary server. An example of such a category of privacy sensitive data are minutes and internal notes. A second certified party may for example not be willing to make these available via the intermediary server, but may not object to make these available directly to the first certified party server of the first party. E.g. the second party would not object to make available to the first party a recording of a telephone call between the second and the first party, but may not be willing to involve the certified intermediary server when sharing this information. The certified intermediary server may provide a single digital signature for the censored copy. In that case, the first certified party server can verify authenticity of the first and the second portion by combining these portions so as to reconstruct the censored copy and by verifying that the digital signature matches this reconstructed censored copy. Alternatively, the second certified party server may provide separate digital signatures for each of the portions of the censored copy. The second certified party server may make available the single digital signature or the respective digital signatures directly to the first certified party server or indirectly via the certified intermediary server. Preferably a digital signature is made available in the same manner as in which the data with which is associated is made available. This is not necessary however. In case the second certified party server selectively makes available copies of privacy sensitive data belonging to a category directly to the first certified party server, it is indeed preferred to directly make available a separate digital signature for this data to the first certified first party server. In this way the second certified party server not only avoids that the certified intermediary server can observe this data, but it also avoids that the certified intermediary server becomes aware of this data.

In embodiments of the method according to the first aspect, the system according to the second aspect and the intermediary server according to the third aspect, the certified intermediary server, upon receipt of the primary request, selects one or more of a plurality of second certified party servers (e.g. B1, B2, B3, B4) as the at least a second certified party server and performs said query procedure with said one or more selected second certified party servers.

In an embodiment thereof, the certified intermediary server makes said selection upon inspection of an availability table that indicates which of the plurality of second certified party servers (B1, B2, B3, B4) can at least partly comply with the primary request.

In an embodiment of this embodiment the certified intermediary server, upon receipt of the primary request issues a censored request requesting the selected one or more of the plurality of second certified party servers to make available a copy of a subset of privacy sensitive data units indicated by the censored request, the indicated privacy sensitive data units including privacy sensitive data units indicated in the digitally signed primary request as well as privacy sensitive data units not indicated in the digitally signed primary request. By including in the censored request indications not present in the primary request, the selected one or more of the plurality of second certified party servers do not know which privacy sensitive data is actually requested in the primary request.

The additional indications, which were not present in the primary request may indicate privacy sensitive data which is non-existent with the selected one or more of the plurality of second certified party servers. In that case the certified intermediary server may allow the response of those second certified party servers to become available to the first certified party server that issued the primary request.

The intermediary server may apply a filter to the received data to exclude certain privacy sensitive data, so as to prevent that it becomes available to the first certified party server. Whereas the availability table indicates which second certified party server is allowed to provide privacy sensitive data to which first certified party server (and/or which first certified party server is allowed to request privacy sensitive data from which second certified party server) the filter may provide exceptions to this general authorization matrix. The filter may for example be used to remove privacy sensitive data provided by a second certified party server, as indicated in the additional indications that were added by the intermediary server.

In an embodiment of the method according to the first aspect, the system according to the second aspect and the intermediary server according to the third aspect, the certified intermediary server makes available a further copy of said censored subset to the authorizing party in addition to making available the copy to the first certified party server. Therewith the authorizing party can verify that that the operation of the intermediary server complies with the provided authorizations. The further copy may be a digitally signed authorized copy including the copy of said censored subset and the digital signature of the at least a second certified party, associated with said censored subset. In some cases it may be desired that the privacy sensitive data is not to be made available to the authorizing party. Examples thereof are private notes, for example exchanged between medical specialists to discuss various diagnosis or treatment options. Such information exchange is important in order to come to an agreement about a final diagnosis but would be confusing and possibly unnecessary distress the authorizing party concerned. In order to restrict access of the authorizing party to the content of the message, while allowing the authorizing party to be automatically copied, the second certified party may encrypt the privacy sensitive data included in the authorized copy using a public key of the first certified party server. In an embodiment the at least a second certified party makes available a message including said copy of said censored subset and the digital signature of the at least a second certified party, associated with said censored subset and further including metadata pertaining to the content and/or the targeted recipient. The intermediary certified party server can then use the metadata to determine if the data can be made available to the first certified party server.

As specified below, the certified intermediary server may have access to a secure storage space wherein the authoring party has specified which privacy sensitive data can be shared between which parties. Accordingly, the authorization includes for a combination of a first party and a second party a specification of the privacy sensitive data allowed to be exchanged.

The authorizing party may impose authorizations to a category of parties or to a particular party. For example an authorization may concern a particular general practitioner as the first party or all general practitioners as the first party. The same applies to the second party indicated in the authorization. For example the second party specified in the authorization may be a particular hospital as the or all hospitals in a certain region. Accordingly the following options may be considered.

| First certified party | Second certified party |
|---|---|
| Particular | Particular |
| Particular | Category |
| Category | Particular |
| Category | Category |

In embodiments of the method according to the first aspect, the system according to the second aspect and the intermediary server according to the third aspect the intermediary server is arranged to identify whether at least one of a first party and a second party indicated in the authorization is a particular party, to encrypt the specification of the privacy sensitive data allowed to be exchanged between that particular party and the other party indicated in the authorization in a manner that requires cooperation of said particular party to decrypt said specification. In this way a substantially increased protection of the specification is obtained, as it is not sufficient for an intruding party to only have access to the contents of the intermediary server. A hacker would need to have access to both the intermediary party server and the particular party server in order to be able to decrypt the specification of the privacy sensitive data allowed to be exchanged.

This provides a substantially increased protection. It is noted that this additional protection is not possible in case that both parties indicated in an authorization are categories. In that case the specification can still be encrypted, but the intermediate server alone should be capable of decrypting the specification without cooperation of other parties. In practice however, this case will be rare, as an authorizing party will generally not tend to generally authorize exchange of privacy sensitive data from a category of first parties to a category of second parties.

BRIEF DESCRIPTION OF THE DRAWINGS

These and other aspects are described in more detail with reference to the drawing. Therein.

DETAILED DESCRIPTION OF EMBODIMENTS

Figure 1:
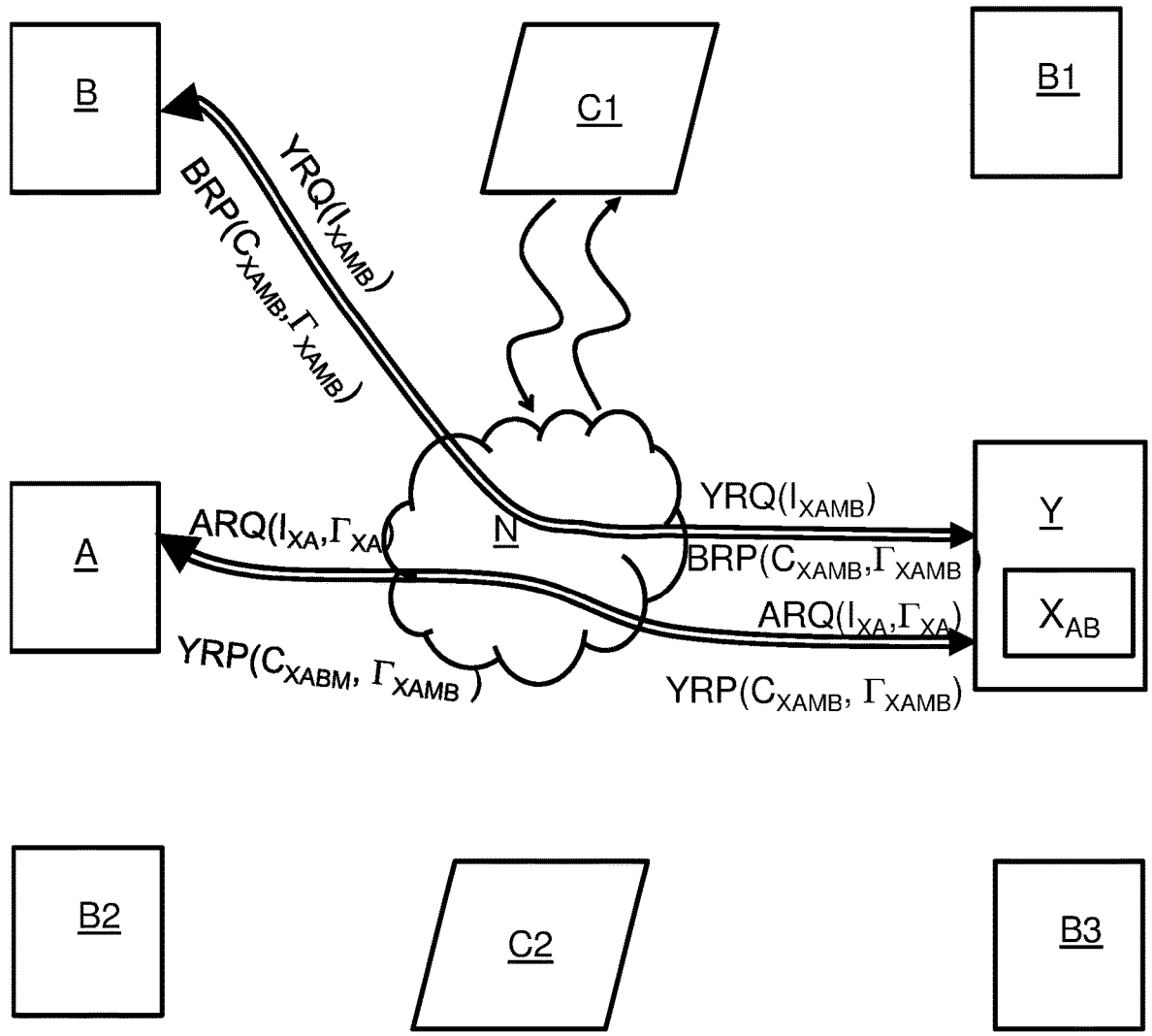
FIG. 1 schematically shows an embodiment of a system according to the invention.

Like reference symbols in the various drawings indicate like elements unless otherwise indicated. The following notation is used in the sequel.

Capitals A, B, Y are used as an indication of the servers, wherein A denotes a data requesting server, B, B1, . . . , Bn denotes a data providing server, and Y denotes an intermediary server.

A request transmitted by a server is indicated as xRQ(p1, p2, . . . , pn), wherein x is a capital A, B, B1, . . . , Bn, Y, indicating the server that issues the request and p1, . . . pn are request parameters as set out in more detail below. Specific requests may include a censored request, e.g. a censored request by the certified intermediary server is denoted as YCRQ( . . . ). Therein the intermediary server requests a data providing server to provide copies of privacy sensitive data unit complying with the authorizations of the authorizing party. A tentative request by the certified intermediary server is denoted as YTRQ( . . . ) and is used to request the provider to provide copies of privacy sensitive data units, not necessarily restricted by authorizations. An availability indication request, denoted as YIRQ( . . . ) is used to request the provider to provide an indication about availability of privacy sensitive data units with the provider. A signature request, denoted as YSRQ( . . . ) is used to request the provider to provide its signature associated with a set of privacy sensitive data units.

A response transmitted by a server is indicated as xRP(p1, p2, . . . , pn), wherein x is a capital A, B, B1, . . . , Bn, Y, indicating the server that issues the response and p1, . . . pn are response parameters as set out in more detail below. Examples of responses by a provider, i.e. a certified second party server are BCRP( ), BTRP( ) and BIRP( ). Therein BCRP denotes a censored response, wherein a certified second party server provides a copy of privacy sensitive data units for which authorization is given. BTRP denotes a tentative response. I.e. authorization for providing the content of the response to the requesting party is not yet confirmed. BIRP denotes a response indicating availability of privacy sensitive data units with the provider, and BSRP denotes a response including a signature by certified party B associated with a set of privacy sensitive data units.

Examples of responses by the certified intermediary server are a censored response YCRP( . . . ), YCCRP( ), and YTRP( . . . ). Therein YCRP( . . . ) is used to denote a censored response obtained from a provider and forwarded to the requesting first certified party. YCCRP( ) denotes a censored response obtained from a provider and forwarded to the requesting first certified party after having confirmed that the censored response indeed complies with the given authorizations. YTRP( . . . ) indicates a verified tentative response. I.e. a forwarded tentative response obtained from a provider after having confirmed that the censored response indeed complies with the given authorizations The notation $I_{subj}$ represents an indication or information about subject, more in particular it is used in the following context:

$I_A$, $I_B$, $I_{Bj}$, $I_Y$: Information about the identity of server A, B, Bj, Y.

$I_X$: Information about data of a person X, e.g. indicating specific data elements.

$I_{XA}$: An indication of privacy sensitive data units about X of which server A requests a copy.

$I_{XAB}$: An indication by server B indicating of which of the privacy sensitive data units indicated by $I_{XA}$ it is prepared to provide a copy.

$I_{XAM}$: An indication by server Y indicating for which of the privacy sensitive data units indicated by $I_{XA}$ authorization is provided by X.

$I_{XAMB}$: An indication by server B indicating of which of the privacy sensitive data units indicated by $I_{XAM}$ it is prepared to provide a copy, or indicating by server Y for which of the privacy sensitive data units indicated by $I_{XAB}$ authorization is provided by X.

The notation $C_{subj}$ represents a copy of a set of privacy sensitive data units, wherein the subscript "subj" is an indication similar to the indication used for the notation $C_{subj}$. For example $C_{XAMB}$ is a copy of privacy sensitive data units provided by server B as indicated by $I_{XAM}$, subject to availability of these privacy sensitive data units with server B and the willingness of server B to provide them.

The notation $\Gamma_{xd}$, denotes an advanced electronic signature, also denoted as digital signature, of a certified party that uses a server x, wherein x is A, B, Bj, and d indicates the set of privacy sensitive data units with which the digital signature is associated, in the same manner as it indicates this for the information symbol I, e.g. d=X indicates the set of all privacy sensitive data units of authorizing party x, and X indicates the set of all privacy sensitive data units of authorizing party x requested by server A, etc. An advanced electronic signature (digital signature) is:

Is uniquely associated with the signer,
Enables an identification of the signer,
Is created with means that can be kept under exclusive control of the signer,
Is associated with the data to which it relates in a manner that enables to detect any change in that data.

In certain embodiments a qualified electronic signature may be used as the digital signature. This is a digital signature that is created with a qualified means and based on a qualified certificate issued by a qualified certification service provider.

It is noted that a digital signature that is associated with set of privacy sensitive data units is also associated with the copy of that set and vice versa, as the digital signature is obtained by a deterministic algorithm, known as such, from a key provided by the signing party and the data. Hence, an (identical) copy of the data results in the same digital signature when also using the same key. A "digital signature" is sometimes considered as a "digital seal" in that it enables the recipient to verify the originator of the message to which it pertains and to verify that it is not modified.

A server's certificate is indicated by "CF", preceded by the capital representing the server, e.g. ACF and BCF are the certificates of servers A and B respectively. A certificate is defined herein as an electronic confirmation that associates validation data with a natural or legal entity. Certificates are issued by a trusted server. For example a certificate is used to determine authenticity of a website and to associate the website with the natural or legal entity to which the certificate was issued.

Symbols S1, S2, . . . , etc indicate procedural steps, possibly having an additional capital, e.g. as in S48A, to indicate an optional step.

FIG. 1 schematically shows a system including a first certified party server A, an certified intermediary server Y and at least one second certified party server B. In the embodiment shown, the at least one second certified party server B is one of a plurality of second certified party servers B, B1, . . . , B3. In practice it will be necessary to use a public communication network N that is also used by entities C1, C2 which may form a risk. In order to mitigate eavesdropping or other undesired interactions by said other entities various security measures are provided as set out below.

The first certified party server is associated with a first party, e.g. a general practitioner or a medical specialist, using the first certified party server. The at least a second certified party server is associated with at least a second party, e.g. another general practitioner or medical specialist, using the at least a second certified party server. The first certified party server A and the certified intermediary server Y are arranged to establish a first secure connection. I.e. a connection wherein these servers verify each others authenticity and exchange encrypted messages.

The at least a second certified party server B and the certified intermediary server Y are arranged to establish a second secure connection as specified above. At least the first certified party server A and the at least a second certified party server B enable the respective parties to digitally sign their messages and to verify each others digital signatures.

Figure 2:
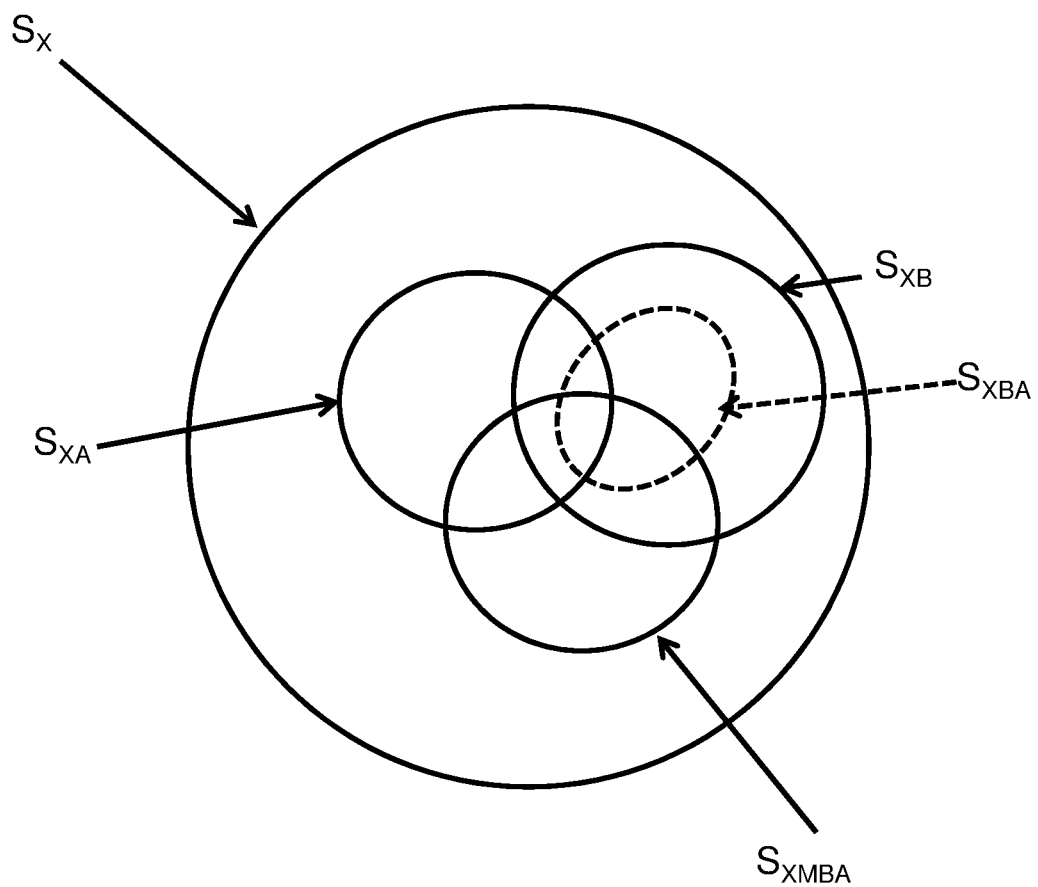
FIG. 2 shows a Venn diagram indicating various sets of privacy sensitive data units and their relations, FIG. 3 schematically shows a method according to the invention, FIG. 4 schematically shows a first embodiment of the method of FIG. 3, FIG. 5 schematically shows a second embodiment of the method of FIG. 3, FIG. 6 schematically shows a third embodiment of the method of FIG. 3, FIG. 7 schematically shows an embodiment of a certified party server for use in a system as shown in FIG. 1, FIG. 8 schematically shows an embodiment of a certified intermediary server for use in a system as shown in FIG. 1.

The first certified party server A is arranged to submit to the certified intermediary server a digitally signed primary request ARQ($I_{XA}$, $\Gamma_{XA}$). including an indication $I_{XA}$ that it requests a copy $C_{XA}$ of a set $S_{XA}$ of privacy sensitive data units subject to authorizations given by an authorizing party, typical a subject X to which the privacy sensitive data units pertain. The set $S_{XA}$ of privacy sensitive data units indicated in the request, may be a subset of the set $S_X$ of all privacy sensitive data units that exist for X, as indicated by the Venn diagram in FIG. 2. Each of the plurality of second certified party servers B, B1, . . . , B3 may have available a subset of the set $S_X$. By way of example the subset $S_{XB}$ of privacy sensitive data units is shown for second certified party server B. It is noted that a second certified party server B may impose restrictions on privacy sensitive data units of this subset $S_{XB}$ of privacy sensitive data. For example, second certified party server B may have a policy to only share copies from the subset $S_{XBA}$ to first certified party server A.

As indicated above, the exchange of copies of privacy sensitive data is controlled by certified intermediary server Y subject to authorizations $X_{AB}$ given by authorizing party X. The certified intermediary server may for example use an authorization control table including a set of indications $I_{AB}$, indicating for each pair of certified party servers A, B associated in the system the subset of privacy sensitive data units for which authorizing party X has authorized certified party server A, B to provide a copy to certified party server B. It is noted that an authorization $X_{AB}$ is not necessarily the same as an authorization $X_{BA}$. I.e. authorizing party X may have authorized copying a certain privacy sensitive data unit from A to B, but may have prohibited copying of that privacy sensitive data unit from B to A.

In the sequel it is presumed that the certified intermediary server already has access to the authorizations $X_{AB}$ from the authorizing party X, e.g. in a secure storage space forming part of that server or controlled by that server. Alternatively the certified intermediary server may request the authorizing party X to provide authorizations on a case by case basis. Alternatively, or in addition it is possible that the authorizing party X changes his/hers authorizations from time to time. In an embodiment, the authorizing party X can specify a time window for an authorization. A time window specified for an authorization indicates within which time frame that authorization is valid. For example X can specify that party A may only receive a certain class of privacy sensitive data form party B within the coming three months. In this way the authorizing party X can enable exchange of that class of privacy sensitive data on a case to case basis while avoiding exchange of such data in the future, even if X forgets to cancel the authorization. Additionally, or alternatively X may specify that a party A may not receive (a class of) privacy sensitive data from party B before a predetermined point in time, therewith avoiding that A has access to very recent privacy sensitive data.

In any case it is important that the authorizing party X should be reliably authenticated in the course of providing and/or changing authorizations, for example by using a Digid code. For those not having access to electronic computation means the authorizations could be provided in writing and authenticated by a signature, possibly including a copy of an personal identification such as a passport. Alternatively, an authorizing party X may have authorized a deputy to provide and/or change authorizations.

The certified intermediary server may e.g. store the authorizations $X_{AB}$ for this example of certified party servers A, B1, ..., B5 as follows:

| Server 1 | A | B1 | B2 | B3 | B4 | B5 |
|---|---|---|---|---|---|---|
| A | — | $X_{AB1}$ | ... | ... | ... | ... |
| B1 | $X_{B1A}$ | — | ... | ... | ... | ... |
| B2 | ... | ... | — | ... | ... | ... |
| B3 | ... | ... | ... | — | ... | ... |
| B4 | ... | ... | ... | ... | — | $X_{B4B5}$ |
| B5 | $X_{B5A}$ | ... | ... | ... | $X_{B5B4}$ | — |

In the embodiment shown the table indicates the subset of privacy sensitive data units for which authorizing party X has given an explicit authorization. Alternatively, the table may indicate the privacy sensitive data units for which X has explicitly prohibited to prepare and transfer a copy. In the latter case an authorization is given implicitly for those privacy sensitive data units that are not indicated. Alternatively, the authorization may be based on more general authorization rules, for example for providing an authorization depending on a quality certificate for an institution associated with a certified party server. Still alternatively, the certified intermediary server Y may explicitly request a certified subject server X associated with authorizing party X to indicate the authorizations.

The exchange of copies of privacy sensitive data is controlled by the certified intermediary server Y subject to authorizations $X_{AB}$ given by subject X. In the embodiment shown, X has specified that only copies of data units in a subset $S_{XB1A}$ are allowed to be provided by second certified party server B1 to first certified party server A. As shown in FIG. 1, in practice a plurality of second certified party servers B1, ..., B5, may be included in the system. Each of these second certified party servers B1, ..., B5 may own its proper subset of privacy sensitive data units of X and have its own policy for making available these privacy sensitive data units to other certified servers. Likewise, the exchange thereof is subject to authorizations given by subject X. It is further noted that a second certified party server B1, ..., B5, can possibly operate as a first certified party server, that submits a primary request to the certified intermediary server including an indication that it requests a copy of a set of privacy sensitive data units. Conversely, the first certified party server may also operate as a second certified party server.

Figure 3:
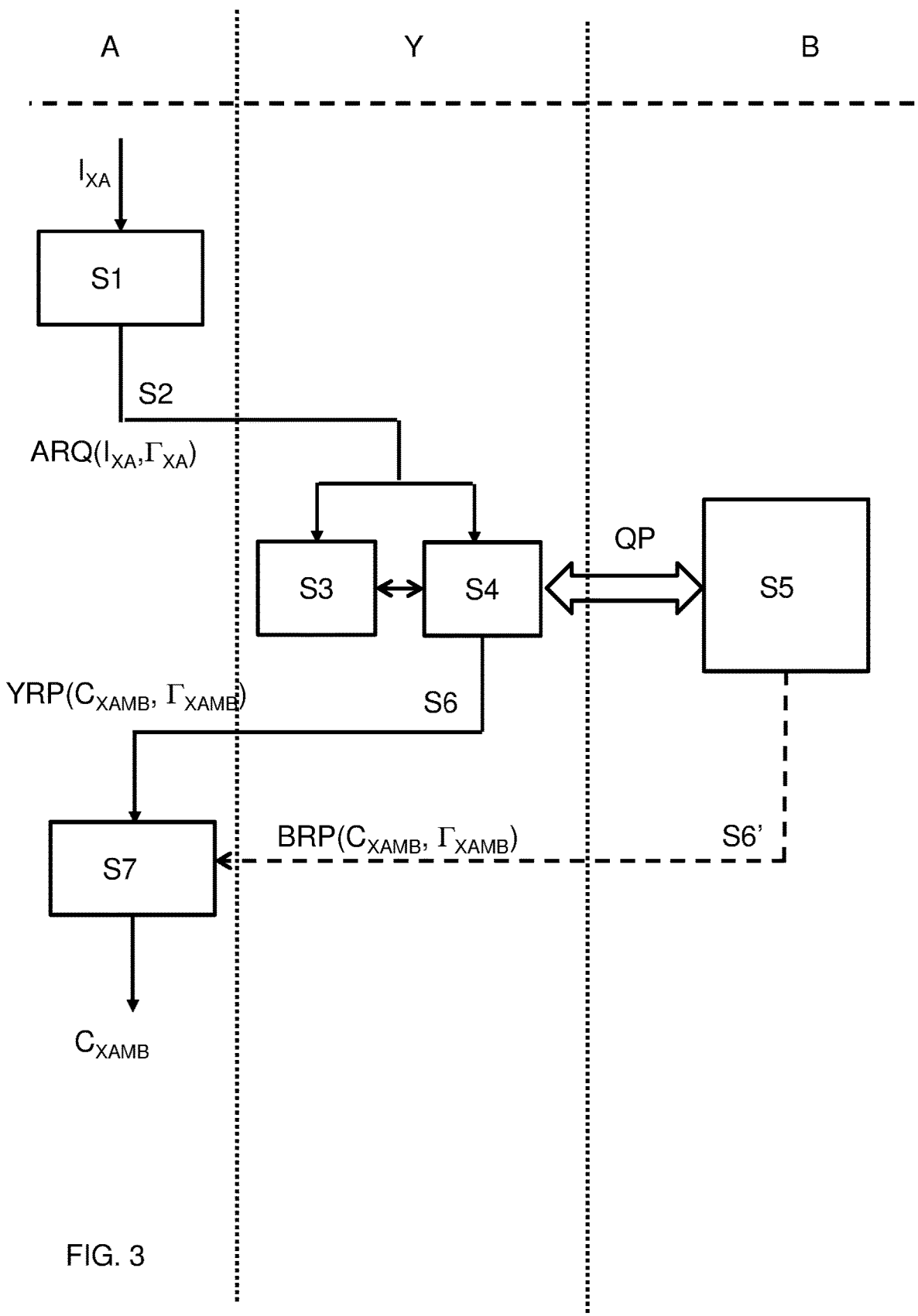

An overview of the procedure is illustrated in FIG. 3. It is presumed herein that that certified party server A is the first certified party server and that certified party server B is the second certified party server. Having established a secure connection, for example as specified in more detail below, in a first step S1, the first certified party server A or a person (e.g. a general practitioner) using the server or using a digital signature preparation device connected to the server, prepares a digitally signed primary request $ARQ(I_{XA}, \Gamma_{XA})$ to certified intermediary server Y. The primary request ARQ $(I_{XA}, \Gamma_{XA})$ includes at least a primary request indication $I_{XA}$ specifying a first set of privacy sensitive data units $X_A$ of which a copy $C_{XA}$ is requested and a digital signature $\Gamma_{XA}$ associated with said primary request indication $I_{XA}$. This enables third parties to reliably confirm that the first certified party server A is indeed the creator of the primary request indication $I_{XA}$. A privacy sensitive data unit is for example an X-ray picture of the authorizing party X or a general practitioners report of a consult with authorizing party X. The primary request indication $I_{XA}$ may indicate such data units individually or may include indications specifying a group of privacy sensitive data units, e.g. the collection of all X-ray pictures for party X, or a collection of consult reports in a specific year.

In step S2, the first certified party server A uses a first secure connection for transmitting the primary request ARQ $(I_{XA}, \Gamma_{XA})$ to the certified intermediary server Y. The secure connection enables the servers using this connection to verify each others authenticity and may provide for encryption of the transmitted messages, for example if the messages created by the servers themselves are not yet encrypted.

The certified servers involved may use a private network to avoid any risk of interception or modification by unauthorized entities. Generally a private network is not available, so that the certified servers typically use a secure communication layer on a public network. Examples thereof are the Transport Layer Security (TLS) and its predecessor, Secure Sockets Layer (SSL), both of which are frequently referred to as 'SSL'. Such a secure communication layer provides for a cryptographic protocol designed to provide communications security over a computer network. The exemplary protocols use X.509 certificates and hence asymmetric cryptography to authenticate the counterpart with whom they are communicating, and to subsequently negotiate a symmetric session key. This session key is then used to encrypt data flowing between the parties. This allows for data/message confidentiality, and a message signature for message integrity. As part of this mutual authentication, the certified servers may submit session cookies, to prevent replay attacks.

In step S3 the certified intermediary server Y determines which authorizations are provided by the authorizing party X for transmission of information concerning privacy sensitive data from the at least a second certified party server B to the first certified party server A. Information concerning privacy sensitive data may include for example an indication about the availability of privacy sensitive data and a copy of privacy sensitive data.

The verification in step S3 may include verifying the digital signatures of both the first certified party server A and at least a second certified party server B received as part of the messages conveyed during the query procedure. The verification of the conveyed digital signatures renders it possible to confirm the identity of the first party, e.g. a GP, using the first certified party server and the second party, e.g. a medical specialist, using the second certified party server. In this way a verified indicator $I_A$, $I_B$ can be provided that reliably indicates the requesting party and the providing party, and these verified indicators can be used to determine which privacy sensitive data units may be copied and transferred from the providing party to the requesting party. In addition the certified intermediary server Y may use the digital certificates of the certified party servers A and B for verification.

Authorizations may be general or specific. I.e. authorizing party X may have authorized transmission of any indications about availability of specific privacy sensitive data units or have authorized transmission of copies of specific privacy sensitive data units from the at least a second certified party server B to the first certified party server A. Alternatively authorizing party X may have authorized transmission of any indications about availability of privacy sensitive data (i.e. any privacy sensitive data unit) or have authorized transmission of any copies of privacy sensitive data from the at least a second certified party server B to the first certified party server A. In addition the authorizations by X may include restrictions as to which extent the at least a second certified party server may be informed about the existence of a request for information about privacy sensitive data units.

In step S4 the certified intermediary server Y uses a second secure connection to execute a query procedure QP The query procedure includes at least making available by the certified intermediary server Y to the at least a second certified party server B the digitally signed primary request $I_{XA}, \Gamma_{XA}$. Normally the query procedure proceeds in that the at least a second certified party server B make available copies of a privacy sensitive data units including at least a copy of a censored subset of privacy sensitive data units, the censored subset comprising the privacy sensitive data units as specified by the primary request indication ($I_{XA}$) subject at least to said authorizations ($X_{AB}$) and subject to availability thereof with the at least a second certified party server. During the query procedure the second certified party server B inspects in a step S5 A's digital signature $\Gamma_{XA}$ to verify authenticity of the primary request. If it determines a lack of authenticity or any other deficiency, it disables completion of the query procedure. The at least a second certified party server B make available a digital signature of said at least a second certified party server B or a person (e.g. a medical specialist) using the server or using a digital signature preparation device connected to the server, associated with the censored subset. This enables third parties to reliable confirm that the party using the at least a second certified party server B is indeed the creator of the copy.

Typically, in a step S6 the certified intermediary server Y uses the first secure connection for transmitting a mediator response YRP($C_{XAMB}$, $\Gamma_{XABM}$) to the first certified party server A. The mediator response includes the digitally signed response $C_{XAMB}$, $\Gamma_{XAMB}$ of the at least a second certified party server B. However, alternatively embodiments may be considered wherein the at least a second certified party server B make available (step S6') a copy of the censored subset as well as its digital signature associated therewith to the first certified party server A, for example as part of a provider response BRP($C_{XAMB}$, $\Gamma_{XABM}$) submitted to the first certified party server A, therewith bypassing the certified intermediary server in this stage. It is preferred however that the certified intermediary server also intermediates in this stage so as to enable additional security verifications.

In step S7, the first certified party server A, receiving the mediator response YRP($C_{XAMB}$, $\Gamma_{XAMB}$) typically inspects the digital signature $\Gamma_{XAMB}$ to verify that second certified party server B is indeed the creator of the copy. In this way the second certified party server A can mitigate the risk of receiving incorrect data.

The purpose of the verification in step S3 is to achieve that transfer of information about privacy sensitive data is subject to the authorizations given by the authorizing party. To that end the certified intermediary server Y needs to reliably determine the identity of the entity from which it receives the primary request and the entity with which it engages in the query procedure. Subsequently it can determine which authorizations are given by the authorizing party for transmitting information by the entity identified as the at least a second certified party server to the entity identified as the first certified party server. This could be in any stage, provided that a first entity A does not receive any information concerning privacy sensitive data of a person X without the authorization of that person. For example the certified intermediary server Y may verify the identities and the authorizations just before a decision is taken whether or not to transmit the mediator response YRP($C_{XAMB}$, $\Gamma_{XAMB}$). In case it is found that an entity involved in the first or the second secure connection is not reliable, and/or no authorization is present, the certified intermediary server Y can still prevent the transmission. For efficiency of the procedure it is however preferred that identities and authorizations are verified as soon as possible. This can avoid unnecessary transmissions.

The query procedure QP may include one or more procedural stages as set out in more detail in the examples presented below.

EXAMPLE 1

Figure 4:
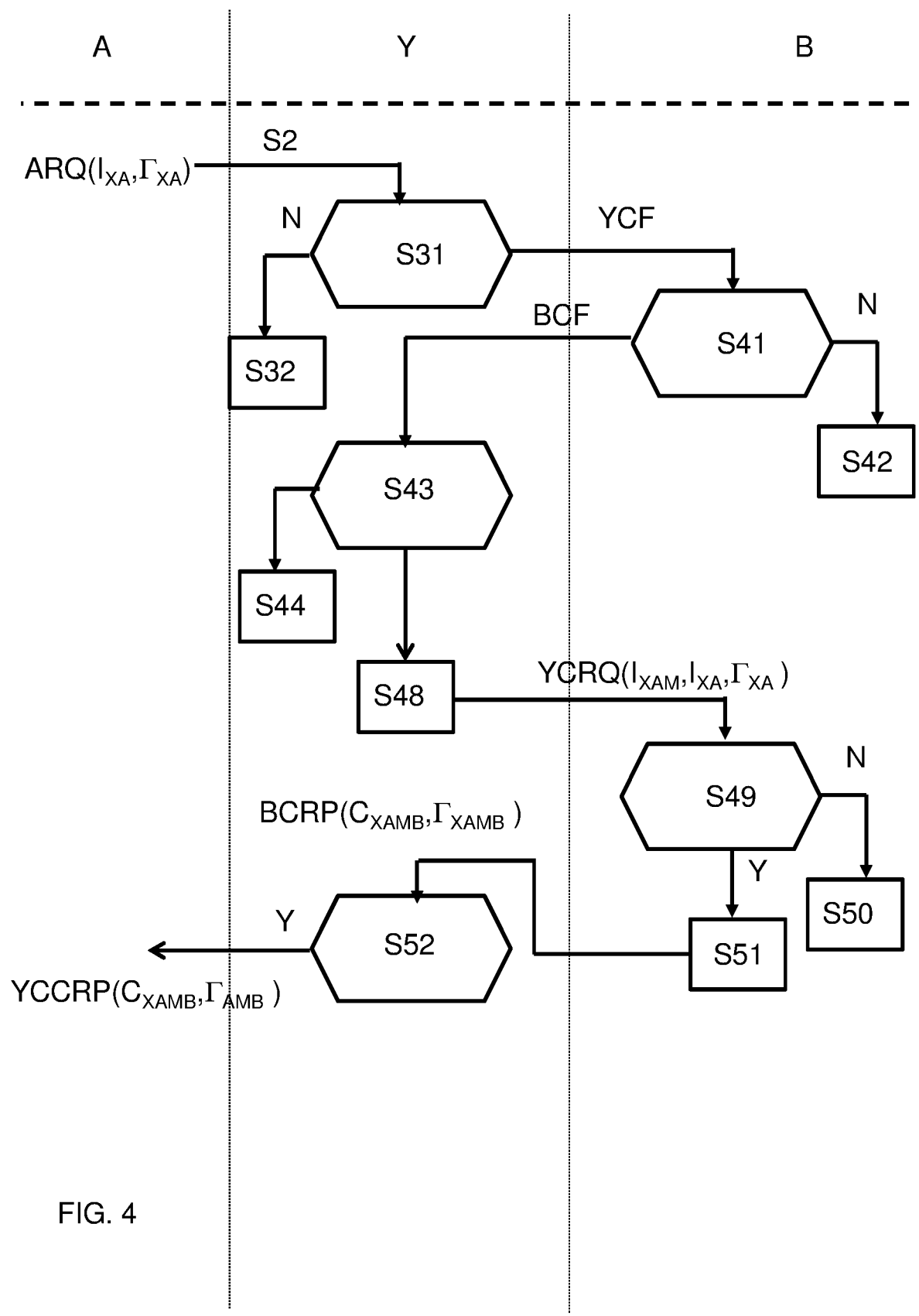

A first embodiment of a method is shown in more detail in FIG. 4

Having received the primary request ARQ($I_{XA}, \Gamma_{XA}$) in step S2, the certified intermediary server Y verifies in a step S31 the identity of the entity from which it receives the request. The verification may include a verification of the certificate given to the first certified party server A. In addition the certified intermediary server Y may verify the digital signature $\Gamma_{XA}$ included in the request. If any deficiencies are found, such as a missing or wrong certificate, and/or a missing or wrong signature, and or a signature that is not consistent with the certificate (branch N), the normal procedure is interrupted. Instead additional security procedures S32 may be performed, e.g. informing security personnel to investigate the matter. Similarly, the first certified party server A may verify credentials of certified intermediary server Y, and take further security steps when necessary.

If no deficiencies are found, the certified intermediary server Y establishes a second secure connection with one or more second certified party servers, in this example second certified party server B. To that end certified party server B verifies that the secure connection actually originated from Y by verifying that its certificate YCF is authentic in step S41. If B detects a deficiency in the certificate YCF it interrupts the procedure, and possibly performs a security procedure S42, for example comparable to the procedure described for step S32. Likewise, Y will verify that it has actually established a connection to second certified party server B by verifying its certificate in step S43. If on its turn Y detects a deficiency in the certificate BCF it interrupts the procedure, and possibly performs a security procedure S44, for example comparable to the procedure described for step S32. If Y detects no deficiency in this step S43, it proceeds with step S48 wherein it initiates the query procedure with second certified party server B.

In step S48, the certified intermediary server Y prepares a censored request YCRQ($I_{XAM}, I_{XA}, \Gamma_{XA}$), which includes the digitally signed primary request $I_{XA}, \Gamma_{XA}$ as received from the first certified party server A and an indication $I_{XAM}$ of the subset of data elements about which the second certified party server is authorized to provide information to the first certified party server A.

In step S49 the second certified party server B verifies the censored request YCRQ($I_{XAM}, I_{XA}, \Gamma_{XA}$), for example by verifying the digital signature $\Gamma_{XA}$ and by verifying that the indication $I_{XAM}$ indeed specifies a subset of the set of privacy sensitive data units as originally requested by A, by the indication $I_{XA}$. If the verification points out that the censored request YCRQ($I_{XAM}, I_{XA}, \Gamma_{XA}$) is suspect, the second certified party server B proceeds with a security procedure, for example the security procedure described for step S32. Otherwise the second certified party server B proceeds with step S51, wherein it transmits a provider response BCRP($C_{XAMB}, \Gamma_{XAMB}$) including the digitally signed censored copy, including the requested copies $C_{XAMB}$ and its digital signature $\Gamma_{XAMB}$. The digitally signed censored copy is valid as digitally signed authorized copy.

As a final safety measure, in step S52, the certified intermediary server may inspect the provider response. The inspection may for example include a verification that the provided copied data does not include any information which is not authorized to be transmitted from the second certified party server B to the first certified party server A and a verification of the signature $\Gamma_{XAMB}$ in the response BCRP($C_{XAMB}, \Gamma_{XAMB}$). Subsequently, provided that no deficiencies are found in step S52, the certified intermediary server transmits to the first certified party server a verified censored response YCCRP($C_{XAMB}, \Gamma_{XAMB}$). The verified censored response includes the digitally signed censored response of the second certified party server B. Therewith the first certified party server A can ascertain that copied privacy sensitive data units received from Y originate from said second certified party server B.

Accordingly, in this embodiment, the certified intermediary server Y transmits to said at least a second certified party server B a censored request YCRQ($I_{XAM}, I_{XA}, \Gamma_{XA}$) for providing a copy of said subset of privacy sensitive data units as indicated by a mediator request indication $I_{XAM}$ included in the censored request, subject to availability thereof with said at least a second certified party server B. Having accepted this censored request YCRQ($I_{XAM}, I_{XA}, \Gamma_{XA}$), the at least a second certified party server has all information it needs to determine which data are requested by the first certified party server and according to the authorizations may be provided by the at least a second certified party server to be received by the at least a first certified party server. For many applications, this is a favorable embodiment, as a single request from the side of the certified intermediary server Y and a single response from the side of the at least a second certified party server suffices to complete the query procedure.

Nevertheless embodiments may be contemplated, wherein it is advantageous to optionally, or structurally include one or more additional stages in the query procedure. For example, a stage may be included wherein the at least a second certified party server B transmits availability information to the certified intermediary server Y. The availability information comprises at least information about availability of privacy sensitive data of the authorizing party X with said second certified party server B. The availability information can be used by the certified intermediary server Y when preparing the request wherein it requests the at least a second certified party server B to provide a copy of privacy sensitive data units as specified in the primary request ARQ($I_{XA}, \Gamma_{XA}$) and subject to the authorizations $X_{AB}$. Therewith it can restrict the request to what is available with the second certified party server B. It is noted that the second certified party server B may restrict the availability information to information only about availability of privacy sensitive data as specified in the primary request. Alternatively however, the availability information provided by the second certified party server B may also include information about other privacy sensitive data that is available with the second certified party server B, for example it may provide an availability indication for all privacy sensitive data units it has for the authorizing party X. Optionally, it may also indicate that it does not have available certain privacy sensitive data units, for example privacy sensitive data units that are known to exist, but that the second certified party server B does not have or is not allowed to deliver according to its own policy.

The availability information may be provided by actually providing copies of available privacy sensitive data units, e.g. as described in Example 2, described below. Alternatively, as set out below in Example 3, the availability information for privacy sensitive data units may be provided as an availability indication, indicating whether or not respective privacy sensitive data units are available with the at least a second certified party server.

EXAMPLE 2

Figure 5:
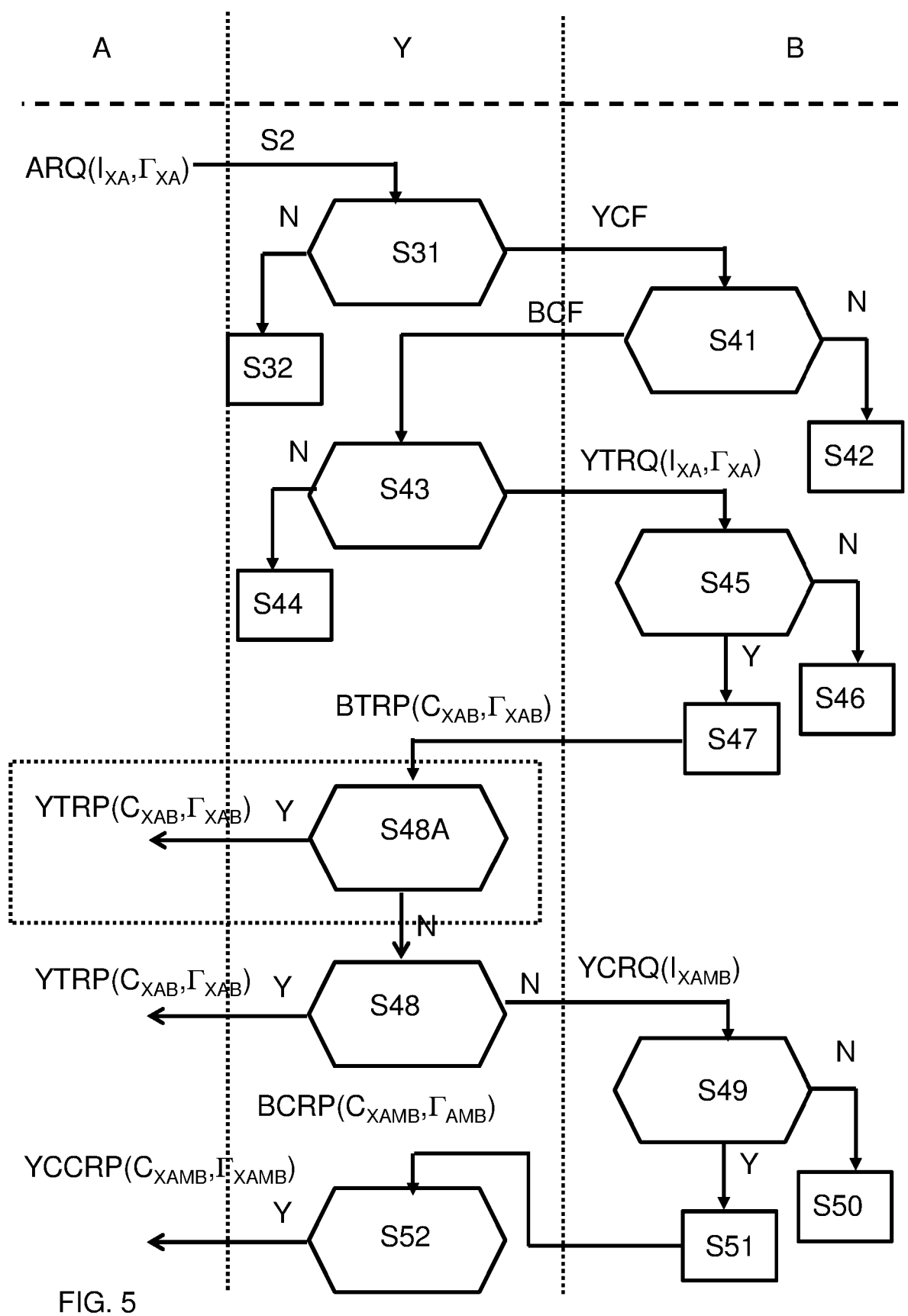

A second embodiment of a method is shown in more detail in FIG. 5. As in the embodiment of FIGS. 3 and 4, the parties involved establish a secure connection, for example according to the same protocols as described with reference to FIG. 3.

As part of a query procedure with the second certified party server B, the certified intermediary server Y transmits a tentative request YTRQ($I_{XA}, \Gamma_{XA}$) to the second certified party B. The tentative request YTRQ($I_{XA}, \Gamma_{XA}$) includes at least the digitally signed primary request $I_{XA}, \Gamma_{XA}$.

In step S45, as part of the query procedure, the second certified party server B verifies the signature $\Gamma_{XA}$ of the digitally signed primary request $I_{XA}, \Gamma_{XA}$. Therewith the second certified party server B can verify that the request indeed originates from first certified party server A, despite the fact that it receives this request from certified intermediary server Y. If the signature $\Gamma_{XA}$ is deficient or lacking, the second certified party server B interrupts the procedure, and possibly performs a security procedure S46, for example comparable to the procedure described for step S32. If B detects no deficiency in this step S45, it proceeds with step S47.

In step S47, as part of the query procedure, the second certified party server B verifies which of the privacy sensitive data units for which a copy is requested by A is in its possession. The second certified party server B may further verify in this step S47, for which of these requested possessed elements it is allowed to provide a copy according to its own policy, which may be a general policy or a specific policy with respect to the first certified party server A. Subsequently the second certified party server B transmits a tentative response BTRP($C_{XAB}, \Gamma_{XAB}$) to the certified intermediary server Y. The tentative response includes a copy $C_{XAB}$ of a second set of privacy sensitive data units and a digital signature of the second certified party associated with the copy. In the present embodiment, the copies are provided of the privacy sensitive data units indicated in said primary request indication ($I_{XA}$) that the second certified party server B is prepared to and can make available to the first certified party server A. The first provider response is digitally signed by a digital signature $\Gamma_{XAB}$ of the second party.

Embodiments may be contemplated wherein the second certified party server does not restrict the content of the tentative response to only copies of privacy sensitive data units indicated in the primary request indication $I_{XA}$ but for example provides the copies of all privacy sensitive data pertaining to the authorizing party, which are in its possession. This may be practical for example in cases where the available privacy sensitive data only consumes a relatively modest amount of memory. This may also be practical if a requesting party often requests a copy of all privacy sensitive data pertaining to an authorizing party X.

Nevertheless, it is preferred to restrict the tentative response to copies of privacy sensitive data units indicated in the primary request. In this case the tentative response can be further processed as an authorized response also if the primary request does not specify all privacy sensitive data units of the authorizing party.

In step S48, as part of the query procedure, the certified intermediary server Y verifies whether or not it is authorized to provide the first certified party server with the copy $C_{XAB}$ included in the tentative response BTRP. This is not the case (N) if the copy $C_{XAB}$ comprises a copy of any privacy sensitive data unit for which no authorization is provided.

The verification in step S48 typically includes a verification of the authenticity of the parties for which the intermediary server mediates the transmission of the copied privacy sensitive data units based upon the authorizations given by the authorizing party. This authenticity verification includes verifying the digital signatures of both the first party and the second party received as part of the messages conveyed during the query procedure. In this way verified indicators $I_A$, $I_B$ can be provided that reliably indicate the requesting party and the providing party, and these verified indicators can be used to determine which privacy sensitive data units may be copied and transferred from the providing party to the requesting party. As an additional security measure, the certified intermediary server Y may verify the digital certificates of the certified party servers A and B.

Should the outcome of the verification in step S48 be affirmative, the query procedure is completed and the certified intermediary server Y transmits a verified tentative response YTRP($C_{XAB}$,$\Gamma_{XAB}$) to the first certified party server. This verified tentative response includes the tentative copy response that the certified intermediary server Y received from the second certified party server B in step S47. As the tentative response $C_{XAB}$, $\Gamma_{XAB}$ includes the digital signature of the second party, its authenticity can be verified by the first certified party server A, despite the fact that it receives the data from the certified intermediary server Y.

If the outcome of the verification in step S48 is negative, the query procedure continues with a next step wherein the certified intermediary server Y transmits a censored request YCRQ($I_{XAMB}$) to the second certified party server B. The censored request YCRQ($I_{XAMB}$) requests the second certified party server to submit copies of privacy sensitive data units as specified by the indication $I_{XAMB}$. These are the remaining set of privacy sensitive data units selected from the privacy sensitive data units as indicated by indication $I_{XA}$ as originally requested by first certified party server A, but subject to at least the authorizations provided by the authorizing party X and the availability of these privacy sensitive data units with the second certified party server B. The privacy sensitive data units as specified in the indication $I_{XAMB}$ may further be subject to restrictions based on information received with the tentative response BTRP($C_{XAB}$,$\Gamma_{XAB}$) provided in step S47 from the second certified party server B.

The response BTRP($C_{XAB}$,$\Gamma_{XAB}$) provided in step S47 may for example include a cost indication for making available certain data items, and step S48 may take this cost indication into account to restrict the censored request. In case of such further restriction, the certified intermediary server may for example initiate a query procedure with another second certified party server that could possible provide the privacy sensitive data units under more favorable conditions.

It is noted that it is not necessary that the censored request specifically restricts the request to the set available from B. I.e. the request may specify $I_{XAM}$, i.e. indicating the set of privacy sensitive data units of which A requests a copy and for which B is authorized to provide that copy should it be available. This can be considered as an implicit version of the request specifying the indication $I_{XAMB}$.

In step S49 the second certified party server B verifies the censored request YCRQ($I_{XAMB}$), for example by verifying that the indication $I_{XAMB}$ indeed pertains to a subset of the set of privacy sensitive data units as originally requested by A, by the indication $I_{XA}$. If the verification points out that the censored request YCRQ($I_{XAMB}$) is suspect, the second certified party server B proceeds with a security procedure, for example the security procedure described for step S32. Otherwise the second certified party server B proceeds with step S51, wherein it transmits a further provider response BCRP($C_{XAMB}$,$\Gamma_{XAMB}$) with a digitally signed censored copy, including the copies $C_{XAMB}$ of the specified privacy sensitive data units which are available, and its digital signature $\Gamma_{XAMB}$ associated with the copies $C_{XAMB}$ In subsequent step S51, in this case completing the query procedure, the at least a second certified party server sends its response BCRP($C_{XAMB}$,$\Gamma_{XAMB}$) to the certified intermediary server Y.

As a final safety measure, in step S52, the certified intermediary server may inspect the provider response BCRP($C_{XAMB}$,$\Gamma_{XAMB}$). The inspection may for example include a verification that the provided copied data does not include any information which is not authorized to be transmitted from the second certified party server B to the first certified party server A and a verification of the signature $\Gamma_{XAMB}$ in the response BCRP($C_{XAMB}$,$\Gamma_{XAMB}$). Subsequently, provided that no deficiencies are found in step S52, the certified intermediary server transmits to the first certified party server a censored response YCCRP($C_{XAMB}$, $\Gamma_{XAMB}$). The censored response includes the digitally signed response of the second certified party server B. Therewith the first certified party server A can ascertain that copied privacy sensitive data units received from Y originate from said second certified party server B.

As an optional step, forming part of the query procedure, the sixth step S48 may be preceded by an intermediate step S48A in which it is verified whether or not the copy $C_{XAB}$ included in the tentative provider response BTRP($C_{XAB}$, $\Gamma_{XAB}$) is empty. If this copy $C_{XAB}$ is empty, the certified intermediary server Y may provide to the first certified party server an empty mediator response YTRP($C_{XAB}$,$\Gamma_{XAB}$), which includes the signed (empty) provider response $C_{XAB}$, $\Gamma_{XAB}$. In this case the further steps S48-S52 can be skipped.

In summary, the embodiment of the method described with reference to FIG. 5 renders it possible to restrict the set of data for which a copy $C_{XAMB}$ is provided after a first response of the second certified party server. In case no restrictions are necessary or in case the second certified party server does not have or want to make available any copies the query procedure can be carried out in a single request response pair $YTRQ(I_{XA}, \Gamma_{XA})$-$BTRP(C_{XAB}, \Gamma_{XAB})$ as in the embodiment described with reference to FIG. 4.

EXAMPLE 3

A further embodiment is described with reference to FIG. 6. The method shown therein differs from the method as described with reference to FIG. 5, in that in step S47, the second certified party server B does not directly transmit the copies $C_{XAB}$ of the privacy sensitive data units it can and is prepared to provide, but instead provides an indication $I_{XAB}$ thereof. Based on this indication the certified intermediary server in step S48 determines if it desires to receive the copies $C_{XAB}$ of the specified the privacy sensitive data units or only a subset thereof. Upon this decision the certified intermediary server Y transmit a censored request YCRQ ($I_{XAMB}$) indicating all or a subset of the privacy sensitive data units for which it requests a copy. The second certified party server B verifies this request in step S49 in a manner similarly as described with reference to FIG. 5. If the request is compliant, it provides its provider response BCRP ($C_{XAMB}, \Gamma_{XAMB}$) with the requested copies $C_{XAMB}$ and digital signature $\Gamma_{XAMB}$. After a final check the certified intermediary server sends its response YCCRP($C_{XAMB}, \Gamma_{XAMB}$) \including the requested copies $C_{XAMB}$ and digital signature $\Gamma_{XAMB}$ to the first certified party server A In summary, the embodiment of the method described with reference to FIG. 6 renders it possible to restrict the set of data for which a copy $C_{XAMB}$ is provided after a first response of the second certified party server. This embodiment is particularly advantageous in case that the restriction can not be made until further information has become available from the second certified party server. In this case the data traffic can be substantially reduced by only providing an availability indication, as compared to the previous embodiment, wherein the certified second party server provides the copies of the specified privacy sensitive data units.

Figure 7:
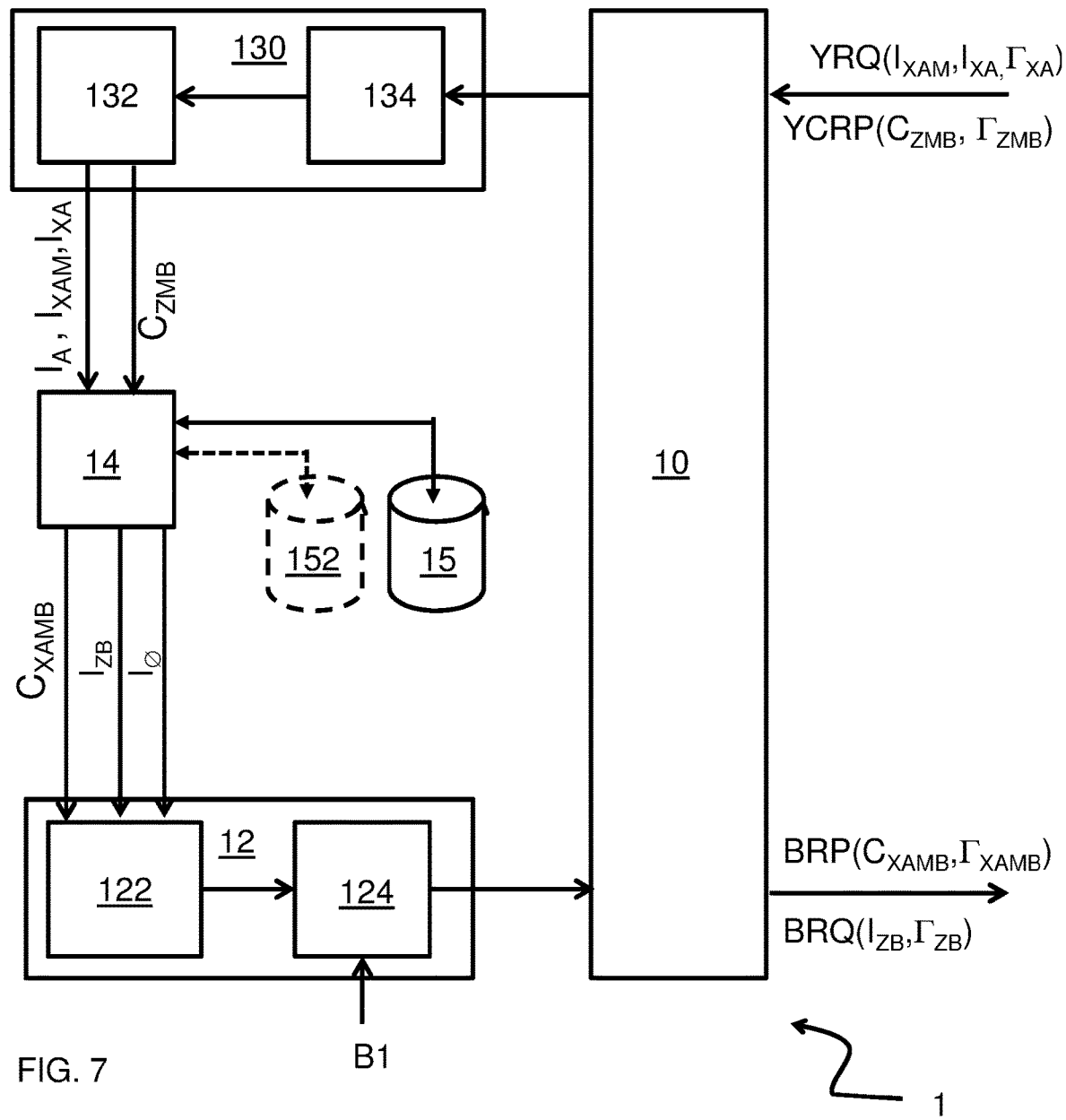

Embodiments may be contemplated, wherein the availability indication is not restricted to the privacy sensitive data units indicated in the primary request. For example the certified party server may provide an availability indication for all privacy sensitive data units pertaining to the authorizing party which it has available. This may be advantageous, in that the certified intermediary server can use the availability indication to construct an availability indication table. This can be used in future cases to select second certified party servers. Two further examples are briefly described with reference to FIGS. 10D and 10E respectively. Certified Party Server FIG. 7 shows an embodiment of a certified party server 1. The certified party server 1 comprises a communication facility 10, an authentication facility 12, an authenticity verification facility 13, a controller 14 and a storage facility 15. The certified party server 1 is configured to operate as a second certified party server B, that selectively provides information about privacy sensitive data to other certified parties upon receipt of a proper request from the certified intermediary server.

In an operational state the communication facility 10 is arranged to establish a secure connection between the certified party server 1 and a certified intermediary server Y for exchanging messages between the certified party server 1 and the certified intermediary server. The messages include at least mediator requests received from the certified intermediary server and provider responses to the certified intermediary server.

The authenticity verification facility 13 is coupled to the communication facility 10. In an operational state it verifies a digital signature in exchanged messages so as to provide verified indications about the origin of the request. In the embodiment shown, the authenticity verification facility 13 receives from the communication facility a mediator request for example a censored request YCRQ($I_{XAM}, I_{XA}, \Gamma_{XA}$) and uses it to provide an indication $I_A$ of the entity that originally submitted the request. The mediator request YCRQ($I_{XAM}, I_{XA}, \Gamma_{XA}$) may include an explicit indication of that entity, but the verification facility 13 has to verify this. A verification of presence and integrity of the signature $\Gamma_{XA}$ is typically carried out by a signature verification module 132 integrated with a decryption module 134. Protocols and keys used for decryption and encryption may be negotiated when initiating a secure connection with the certified intermediary server. The verified identity indication $I_A$, the indication $I_{XA}$ of the requested privacy sensitive data units and the possible indication $I_{XAM}$ of a restriction therein is provided to a privacy sensitive data management unit 14.

Provided that no deficiencies are detected, the privacy sensitive data management unit 14 provides copies $C_{XAMB}$ of available privacy sensitive data units from the storage facility 15. The privacy sensitive data management unit 14 may further restrict what is provided based on its own policy, for example subject to conditions stored in further storage space 152.

The privacy sensitive data management unit 14 provides the copies $C_{XAMB}$ to authentication facility 12, which encrypts (module 122) the provided copies and adds (module 124) B's signature $\Gamma_{XAMB}$. The communication facility then transmits the signed copy as a provider response BCRP($C_{XAMB}, \Gamma_{XAMB}$) to the certified intermediary server.

In the embodiment shown the certified party server handles a request for information concerning privacy sensitive data units in a query procedure comprising a single interaction. Therein it receives a single request YCRQ($I_{XAM}, I_{XA}, \Gamma_{XA}$) that includes a verifiable request from a first certified party server. The single request in addition includes an indication $I_{XAM}$ that indicates whether or not this verifiable request is subject to restrictions by an authorizing party, and if so to what extent restrictions apply.

Alternatively, the query procedure carried out by the certified party server may involve more than one interaction. For example it may receive a tentative request YTRQ($I_{XA}, \Gamma_{XA}$) as a first message from the certified intermediary server, including a verifiable request from a first certified party server, and a censored request YCRQ($I_{XAMB}$) as a second message. The latter may include the indications $I_{XAMB}$ of the restrictions imposed by the authorizing party. In the absence of restrictions the second message may be optional. Preferably however a second message is mandatory to avoid the undesired delivery of data in the inadvertent situation that certified party server does not receive a second message due to other reasons.

In an embodiment, the certified party server is configured to receive a tentative request YTRQ($I_{XA}, \Gamma_{XA}$) as a first message from the certified intermediate server and respond with a tentative response BTRP($C_{XAB}, \Gamma_{XAB}$) including the copies of the privacy sensitive data units indicated in the first message that certified party server 1 is capable and prepared to supply. In this way further transactions are avoided if no restrictions are imposed by the authorizing party, while providing the option for certified intermediary server to submit a restricted request in the same query procedure. In the latter case the certified party server 1 responds by submitting a censored response BCRP($C_{XAMB}$, $\Gamma_{XAMB}$) including the copies $C_{XAMB}$ of privacy sensitive data units which are not subject to the restriction.

In another embodiment, the certified party server is configured to respond to an availability indication request YIRQ($I_{XA}$, $\Gamma_{XA}$) as the first message from the certified intermediate party by submitting a response BIRP($I_{XAB}$, $\Gamma_{XAB}$) including an indication $I_{XAB}$ indicating which of the privacy sensitive data units indicated in the first message YIRQ($I_{XA}$, $\Gamma_{XA}$) the certified party server 1 is capable and prepared to supply a copy. This leaves the option for the certified intermediary server to submit a restricted request later in the same query procedure, while limiting the data traffic in the first part of the query procedure. In the latter case the certified party server 1 responds by submitting a second response BCRP($C_{XAMB}$, $\Gamma_{XAMB}$) including the copies $C_{XAMB}$ of privacy sensitive data units which are not subject to the restriction.

In the embodiment shown the certified party server is further configured to provide a provider response in case the subset of privacy sensitive data for which it is authorized to provide a copy and which it has available is an empty set. In that case the provider response comprises as the digitally signed authorized copy an indication $I_{\varnothing}$ indicating that the subset is empty and its digital signature $\Gamma_{\varnothing B}$ associated with the indication $I_{\varnothing}$.

In the embodiment shown the certified party server 1 is also configured to operate as a first certified party server. In that case, the controller 14 generates a request indication $I_{ZB}$, indicating of which privacy sensitive data units a copy is requested. The authentication facility 12, then encrypts the provided request indication $I_{ZB}$, and adds B's signature $\Gamma_{ZB}$. The communication facility then transmits the signed request BRQ($I_{ZB}$, $\Gamma_{ZB}$) to the certified intermediary server. Upon receipt of the response message YRP($C_{ZMB}$, $\Gamma_{ZMB}$) from the intermediary server, it verifies and decrypts the message and if it is compliant stores the transmitted copies $C_{ZMB}$ in its storage space 15.

Certified Intermediary Server

Figure 8:
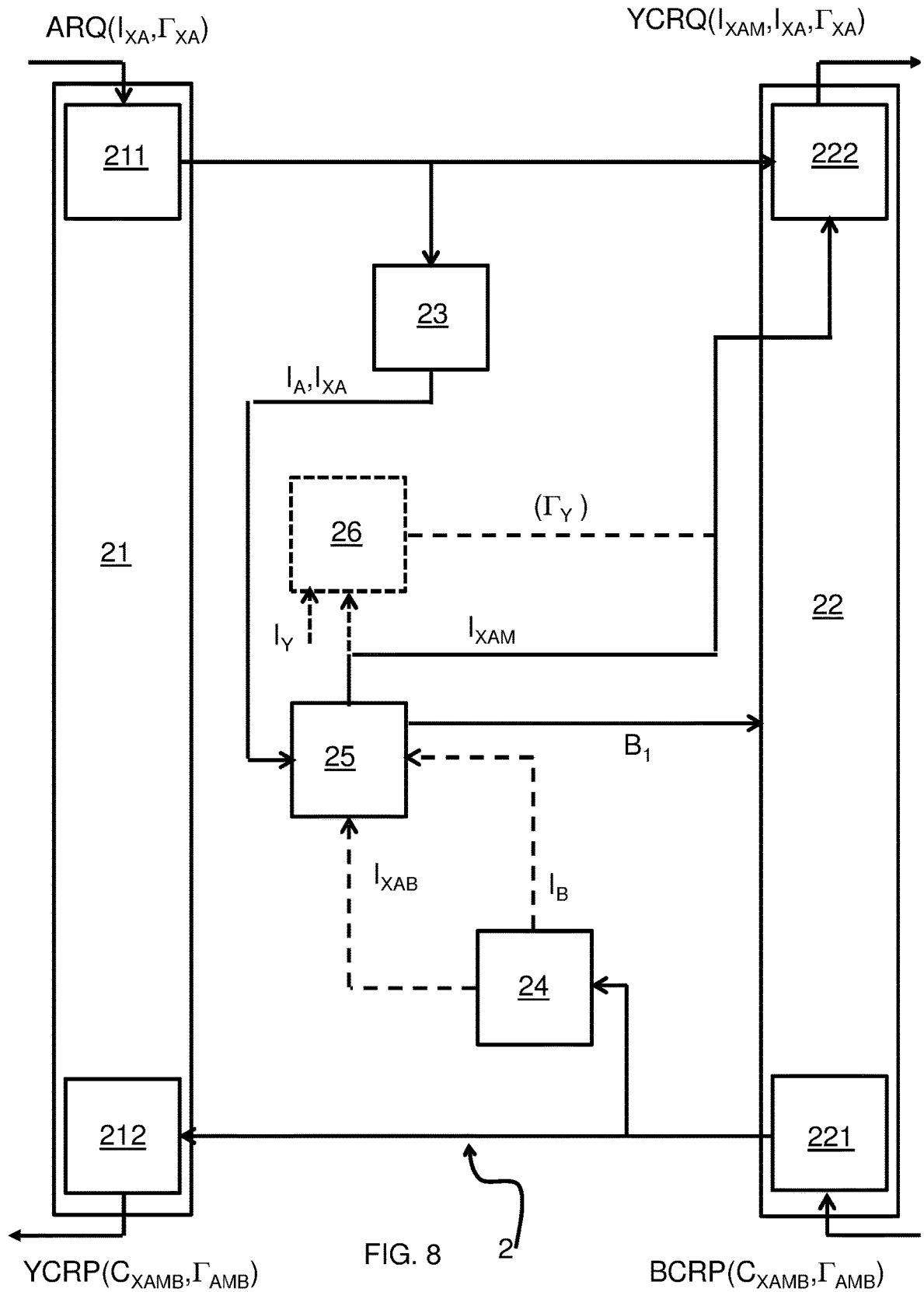

FIG. 8 shows an embodiment of a certified server 2 which is organized to operate as a certified intermediary server Y for controlling exchange of privacy sensitive data units between a first certified party server A and at least a second certified party server B, subject to authorizations $X_{AB}$ imposed by an authorizing party X as illustrated in FIG. 1. The certified intermediary server 2 comprises a communication facility 21, 22, an authenticity verification facility 23, 24, and an exchange authorization controller 25.

The communication facility 21,22 is configured to establish a first secure connection between the first certified party server A and the certified intermediary server 2 for exchanging first messages between the first certified party server and the certified intermediary server 2.

The communication facility 21, 22 is also configured to establish a second secure connection between the certified intermediary server 2 and one or more second certified parties for exchanging second messages between these second certified party servers B and the certified intermediary server 2.

For clarity the drawing shows the communication facility 21, 22 as separate units for communicating with the first certified party server A and a second certified party server B.

In practice a single unit may be used to communicate both with the first certified party server and with the second certified party servers. Further, as described with reference to FIG. 7, depending on the situation a certified party server may in one situation operate as a first certified party server, wherein it requests information, and may in another situation operate as a second certified party server wherein it provides requested information.

In an operational state, the communication facility 21 may receive a primary request ARQ($I_{XA}$,$\Gamma_{XA}$) from a first certified party server A, that includes at least a primary request indication $I_{XA}$ specifying a first set $S_{XA}$ of privacy sensitive data units for which a copy $C_{XA}$ is requested. The primary request is digitally signed by a digital signature $\Gamma_{XA}$ of the first party. Therein block 211 of the communication facility 21 represents a module which handles receipt of the primary request ARQ($I_{XA}$,$\Gamma_{XA}$).

The communication facility 21, 22 is further configured to execute a query procedure in which one or more second certified party servers B are requested to submit copies of privacy sensitive data units as specified by the indication $I_{XA}$ subject to at least the authorizations $X_{AB}$ provided by the authorizing party X.

The query procedure includes transmitting the digitally signed primary request to the involved second certified party servers B and receiving a provider response including the available authorized copies of privacy sensitive data units, digitally signed by a digital signature of the second party involved. The query procedure may be executed as a single request response interaction. Alternatively however additional interactions may take place depending on the particular application and the circumstances of the case.

In this example block 222 of the communication facility 22 represents a module which handles transmission of requests and other messages to the one or more second certified party servers B. Block 221 of the communication facility 22 represents a module which handles receipt of responses from second certified party servers B and possibly other messages.

The communication facility is further configured, using block 212 to transmit to the first certified party server a mediator response that includes the digitally signed response of the second certified party server B.

In operation, when receiving a primary request ARQ($I_{XA}$, $\Gamma_{XA}$) from a first certified party server A, the certified intermediary server determines which second certified party servers B could have the requested privacy sensitive data units available and if so, determines to which extent the authorizing party X has given authorizations to transfer information about the requested privacy sensitive data units from the second certified party servers B to the first certified party server. It has to prevent any non-authorized transmission of transfer of exchange of information about privacy sensitive data units from the second certified party servers B to the first certified party server. To that end it is necessary that certified intermediary server reliably identifies the entities involved when intermediating the transfer of privacy sensitive data. In the embodiment shown the authentication verification facility includes a first module 23 that verifies the signature $\Gamma_{XA}$ of the first certified party server A that should be included in the primary request ARQ($I_{XA}$,$\Gamma_{XA}$). As an additional security measure it may verify a certificate of the first certified party server A. The first module 23 of the authentication facility renders an output signal $I_A$ that indicates the verified identity of the first certified party server A.

In the embodiment shown the authentication verification facility further includes a second module 24 that verifies the identity of the second certified party server. It may verify the identity at the time of establishing the secure connection with the second certified party server B. This verification is possible before transmission of a request to the second certified party server B. Upon completion of the query procedure the certified intermediary server may again verify B's identity by verifying the signature $\Gamma_B$ of the second certified party server B that should be included in the provider response, e.g. BCRP($I_{XAMB},\Gamma_{XAMB}$), BTRP($I_{XAMB}, \Gamma_{XAMB}$).

Although for clarity the authentication verification facility is illustrated as a first module 23 to verify the identity of the first certified party server A and a second module 24 to verify the identity of the second certified party server B, in practice a single module may suffice for this purpose.

Based on the verified identities $I_A$, $I_B$ of the first and the second certified party server involved, the exchange authorization controller 25 determines which transactions are authorized between these certified party servers by the authorizing party. In particular it provides an indication $I_{XAM}$ that indicates which privacy sensitive data units, referred to in the indication $I_{XA}$ in the primary request may be copied by the second certified party server B and transmitted to the first certified party server A. In case more second certified party servers are involved, the exchange authorization controller 25 provides a proper indication for each of these second certified party servers. Depending on the nature of the privacy sensitive data that is requested the exchange authorization controller 25 may select different second certified party server as the possible provider of the copied privacy sensitive data. The exchange authorization controller 25 then inspects the primary request and determines a partitioning wherein each of the addressed second certified party servers is requested by an indication $I_{XAMB1}$, $I_{XAMB2}$, ..., $I_{XAMBn}$ to provide copies of a respective subset of the data indicated in the primary request. To that end the exchange authorization controller 25 may include a content table indicating the availability of privacy sensitive data with second certified party servers.

Once the exchange authorization controller 25 has determined which second certified party server(s) should provide the requested copies, has established a secure connection with these second certified party server(s) and verified their identity/identities, it transmits the mediator request, for example censored requests YCRQ($I_{XAM}$, $I_{XA},\Gamma_A$) to the second certified party server(s) involved.

Upon receiving a response e.g. censored responses BCRP ($C_{XAMB}$, $\Gamma_{XAMB}$) or BCRP($C_{XAMB}$, $\Gamma_{XAMB}$) from the addressed second certified party server(s), the certified intermediate server may verify, e.g. in module 25 that the second certified party server did not supply information for which no authorization was given. It may further verify the signature $\Gamma_B$ of the second certified party server that should be included in its response. If the response received from the second certified party server is compliant it provides its mediator response for example, the censored response YCRP($C_{XAMB}$, $\Gamma_{XAMB}$) to the first certified party server.

In case the certified intermediate server receives responses $B_jRP(C_{XAMBj}, \Gamma_{XAMj})$, or $B_jCRP(C_{XABjM}, \Gamma_{XABjM})$ from a plurality J of second certified party servers j=1 to J, it may either transmit the conveyed data in a mediator response one by one or supply a mediator response in which it collects the supplied information, e.g. YCRP ($C_{XAMB1}$, $\Gamma_{XAMB1}$; $C_{XAMB2}$, $\Gamma_{XAM2}$; ... ; $C_{XAMBJ}$, $\Gamma_{XAMJ}$), or YCRP ($C_{XAB1M}$, $\Gamma_{XA1M}$; $C_{XAB2M}$, $\Gamma_{XAB2M}$; ... ; $C_{XABJM}$, $\Gamma_{XABJM}$).

As schematically shown in FIG. 8 by dashed block 26, the certified intermediary server may also include a digital signature $\Gamma_Y$ associated with the indication $I_{XAM}$, enabling the second certified parties an additional verification of requests received from the certified intermediary server. This is not strictly necessary, as the second certified party servers can verify the certificate of the intermediate certified server.

Figure 6:
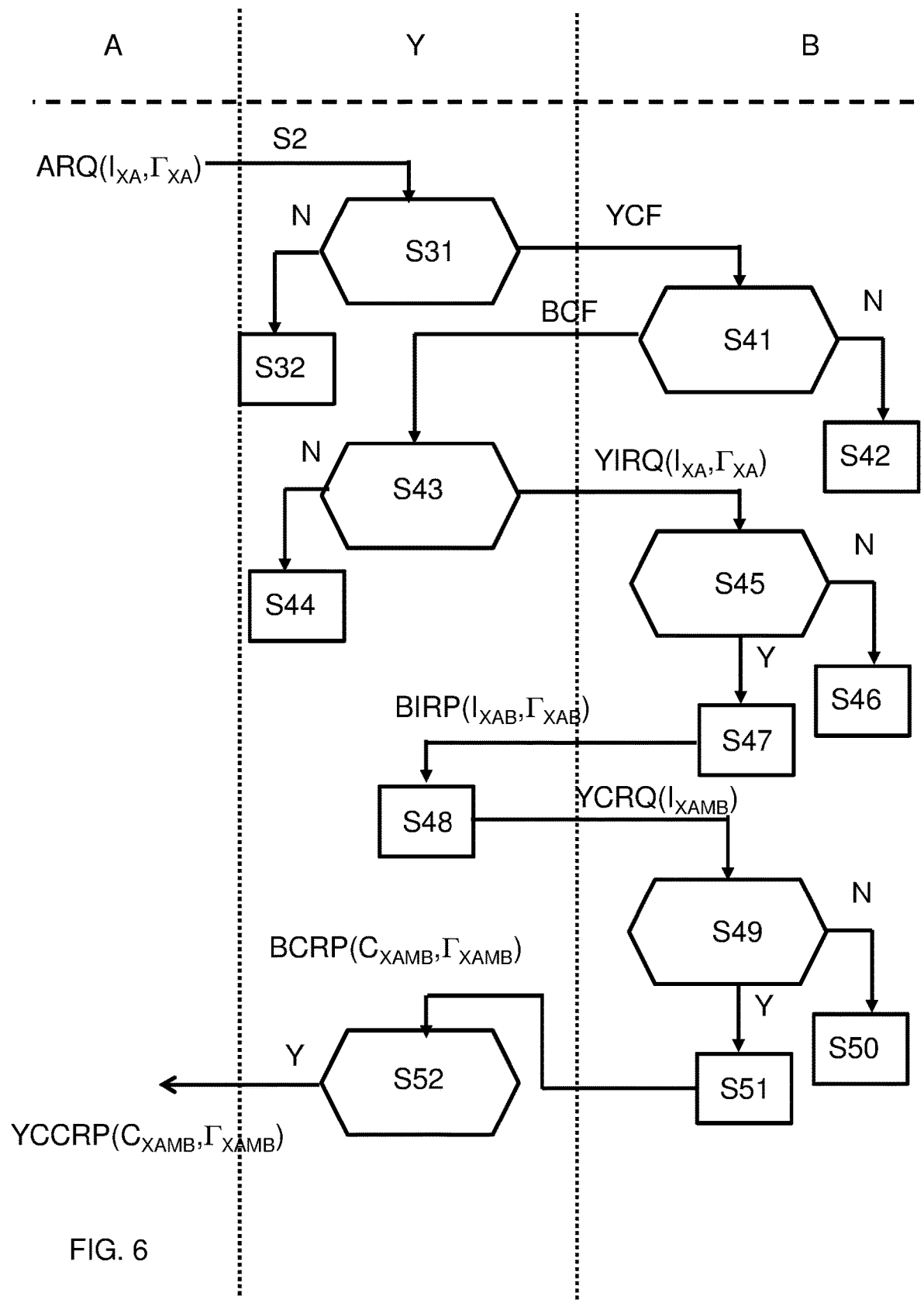

As set out with reference to FIGS. 5 and 6 for example it is not necessary that the query procedure between the certified intermediary server 2 and a second certified party server is limited to a single request—response interaction. In accordance with the procedure described with reference to FIG. 5, the certified intermediary server 2 may for example be configured to request the second certified party server to provide the data as specified in the primary request and optionally issue a second, restricted request as part of the query procedure if upon receipt of the first response from the second certified party server it decides that a restriction is necessary or desired.

Alternatively, in accordance with the procedure described with reference to FIG. 6, the certified intermediary server 2 may for example be configured to request the second certified party server to provide an indication of availability of the data as specified in the primary request and issue a second request as part of the query procedure to provide the available data, possibly subject to a restriction is necessary.

Figure 9:
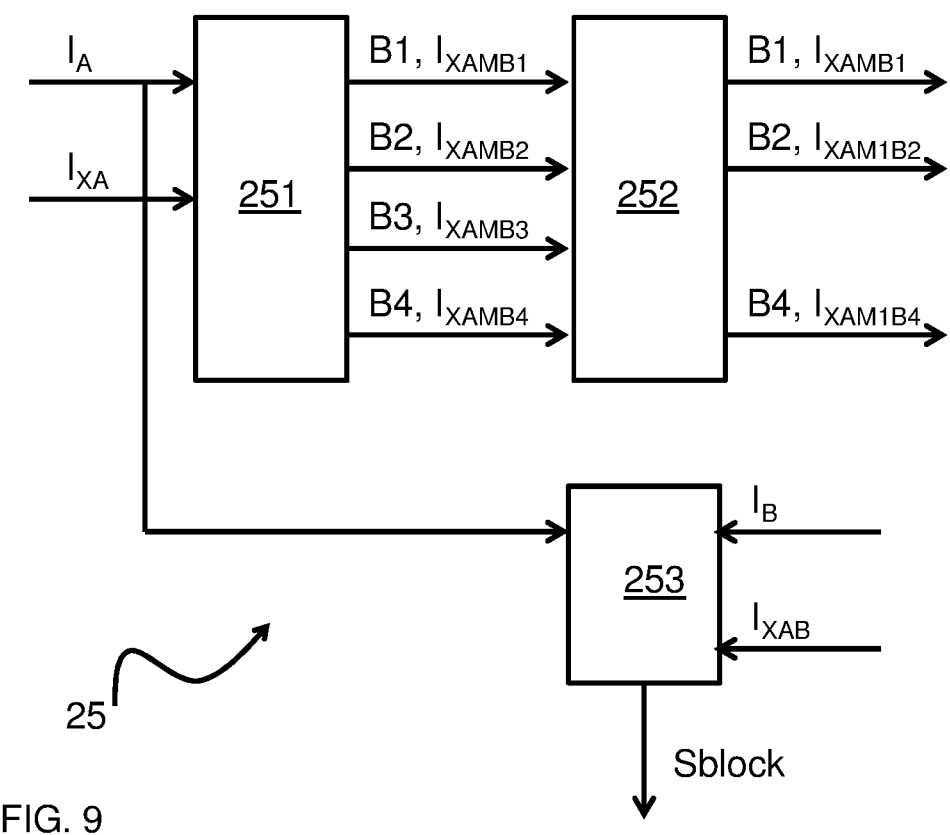
FIG. 9 shows an example of a part of the embodiment of the certified intermediary server of FIG. 8

FIG. 9 shows an example of an exchange authorization controller 25 in an embodiment of a certified intermediary server. In this example the exchange authorization controller 25 includes an authorization selection module 251 that is configured to identify one or more selected second certified parties of a plurality of second certified party servers that are authorized to provide respective subsets of the privacy sensitive data units indicated in the primary request indication to said first certified party server.

In the example shown the authorization controller receives the verified identity indicator $I_A$ of the first certified party that requested a copy of privacy sensitive data elements of subject X indicated by indicator $I_{XA}$. In response to this information the authorization selection module 251 indicates that second certified party servers B1, B2, B3, B4 respectively are authorized to provide copies of privacy sensitive data units indicated by $I_{XAB1}$, $I_{XAB2}$, $I_{XAB3}$, $I_{XAB4}$. The authorization selection module 251 may for example have a lookup table that indicates for each pair of certified party servers which exchanges of information about privacy sensitive data units are authorized.

The authorizations that are provided by the authorizing party may include an end time indication specified for a set of privacy sensitive data units, indicating an end time. In an embodiment the exchange authorization controller is further configured to prevent a direct or indirect transmission of copies of privacy sensitive data units of said set from said second certified party server to the first certified party server if it determines that a current point in time is later than that end time.

Similarly, the authorizations that are provided by the authorizing party may include a begin time indication specified for a set of privacy sensitive data units, indicating a begin time. In an embodiment the exchange authorization controller is further configured to prevent a direct or indirect transmission of copies of privacy sensitive data units of said set from said second certified party server to said first certified party server if said certified intermediary server determines that a current point in time is earlier than said begin time.

The set of privacy sensitive data units for which an end time and/or a begin time is specified may involve all privacy sensitive data units which could potentially exist for the authorizing party X. Alternatively, a begin and/or end time may be specified for a certain class of privacy sensitive data, a particular privacy sensitive data unit or not at all.

In the example shown the exchange authorization controller 25 comprises an availability selection module 252 that is configured to identify one or more selected second certified parties of a plurality of second certified parties that are capable and prepared to provide respective subsets of the privacy sensitive data units indicated in the primary request indication to said first certified party server. In this example the availability selection module 252 receives from the authorization selection module 251 the information indicating which second certified party servers are authorized and to what extent. The availability selection module 252 further determines which of the indicated second certified party servers are actually capable and prepared to provide the specified information. The availability selection module 252 may for example use a lookup table for this purpose that indicates the availability of certain privacy sensitive data units with the second certified parties, as well as their policy in actually delivering this information to others. The lookup table may also include other information, for example about fees charged by the second certified parties for providing copies of privacy sensitive data units. The content of such a lookup table as used by availability selection module 252 may be obtained by earlier negotiations between the certified parties but may alternatively or in addition be obtained on the fly from provider responses.

In the example shown, the availability selection module 252 determines that one of the second certified party servers B3, is not capable or prepared to provide the requested copies indicated by indicator $I_{AXMB3}$, and prepares modified mediator request indications $I_{AXM1B2}$, $I_{AXM1B4}$, in order to obtain these copies from second certified party servers B2 and B4. In this example the mediator request indication for second certified party server B1 is equal to the indication $I_{AXMB1}$ provided by the authorization selection module.

The communication facility 22 then uses the (possibly modified) mediator request indications $I_{AXMB1}$, $I_{AXM1B2}$, $I_{AXM1B4}$ to execute the query procedure with the selected second certified parties B1, B2, B4.

Alternatively, the exchange authorization controller 25 may first verify availability of privacy sensitive data units in the request and subsequently determine whether, and if so, to what extent second certified party servers are authorized to provide copies or other information about the privacy sensitive data units they have available.

Still according to another alternative the exchange authorization controller 25 may verify in a single stage which second certified party servers are authorized, capable and prepared to provide copies or other information about the privacy sensitive data units as specified in the primary request indication.

In certain embodiments the exchange authorization controller 25 comprises a verification module 253 that is configured to check whether the certified intermediary server is authorized to transmit to the first certified party server a mediator response YCRP($C_{XAMB}$, $\Gamma_{XAMB}$) that includes the digitally signed response of said at least a second certified party server B.

The verification module 253 can be provided as an alternative or in addition to the authorization selection module 251. If an authorization selection module 251 is present, the verification module 253 is not essential, as the authorization selection module 251 will have the certified intermediary server requests second certified party servers to provide information about privacy sensitive data units to the extent that they are authorized to do so. However, the verification module 253 may still serve as a fail safe measure in exceptional cases, for example if a second certified party server provides information about privacy sensitive data units for which it is not authorized due to a communication error. The verification module 253 also provides an additional safeguard against attempts by third parties to have second certified party servers deliver other information than requested or authorized, In the example shown the verification module 253 receives the indications $I_{B1}$, and $I_{XAB1}$, indicating a second certified party server B1 that a provided a response and the privacy sensitive data units of which the response includes a copy respectively. In case verification module 253 determines non-compliance with the authorization and/or requests it blocks transmission of the content in the response to the first certified party server.

Figures 10A, 10B, 10C:
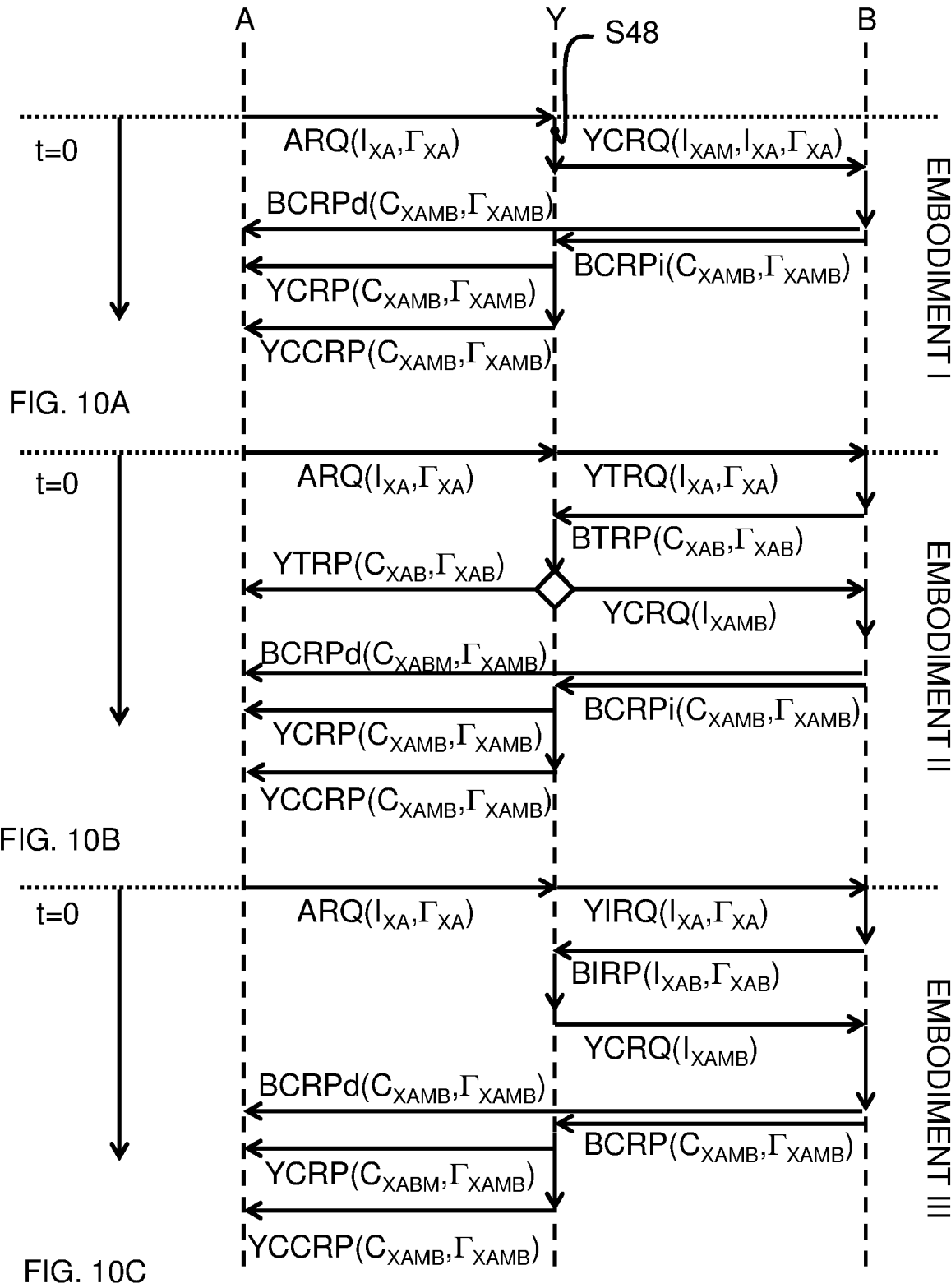
FIG. 10A-E schematically illustrate various options for a query procedure.

FIG. 10A-E schematically illustrate various options. Therein FIG. 10A is an illustration of the first exemplary embodiment, wherein the query procedure comprises a single request-response pair. I.e. the certified intermediary server issues a censored request YCRQ and the certified second party makes available a digitally signed censored copy. It may make available this copy directly to the certified first party server, e.g. by a message BCRPd. Alternatively, it may make available this copy for the first certified party server, by providing it to the certified intermediary server. The certified intermediary server may directly forward the digitally signed censored copy as a response YCRP to the first certified party server or may verify compliance before it submits a verified response YCCRP.

FIG. 10B is an illustration of the second exemplary embodiment, wherein the certified intermediary server first issues a tentative request YTRQ. In response thereto the second certified party server provides a tentative response BTRP. If this is compliant with the authorizations, the certified intermediary server forwards this as a mediator response YTRP to the first certified party server. Otherwise the certified intermediate server proceeds by issuing a censored request YCRQ. From that point the procedure continues substantially analogous to that which is described for the first exemplary embodiment.

FIG. 10C is an illustration of the third exemplary embodiment, wherein the certified intermediary server first issues an availability indication request YIRQ. In response thereto the second certified party server provides an indicative response BIRP, providing indications about available privacy sensitive data units. The certified intermediary server may subsequently use this information when it issues a censored request YCRQ. Subsequently the second certified server can respond to the censored request for example as described with reference to FIG. 10A.

Figure 10D:
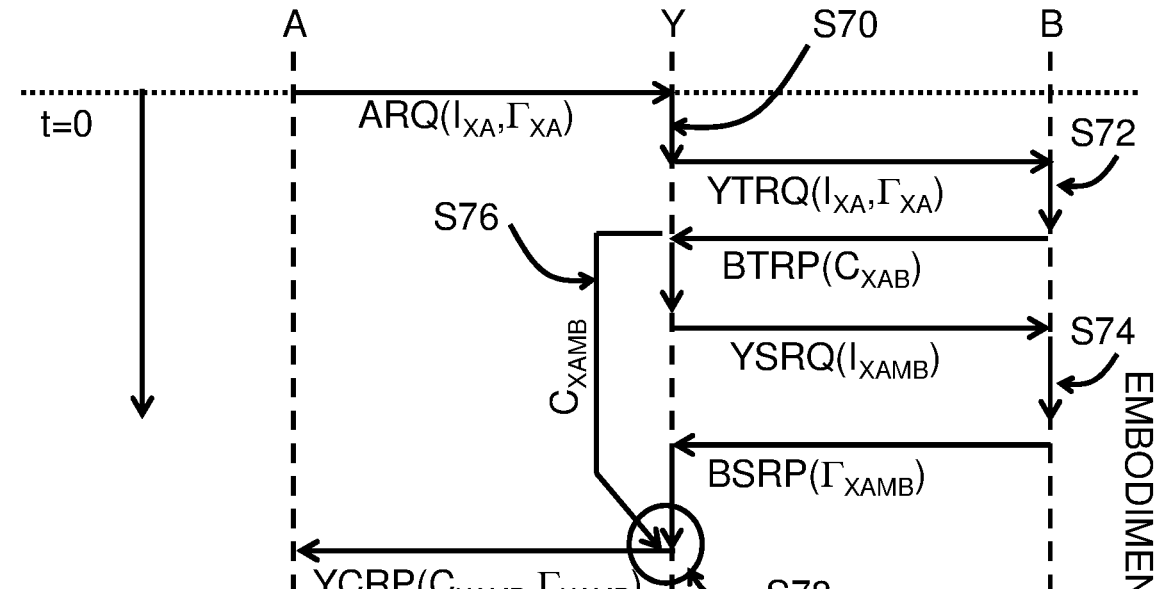

FIG. 10D shows a further exemplary embodiment. As in exemplary embodiment II described with reference to FIG. 10B, the intermediary server issues a tentative request YTRQ($I_{XA}$,$\Gamma_{XA}$), without imposing restrictions determined by authorizations. Issuing the tentative request is typically subject to confirmation in a preceding verification step (S70) that the digitally signed primary request is authentic. The at least a second certified party server in its turn verifies (S72) whether the tentative request complies with all requirements and if so, responds by making available a tentative copy ($C_{XAB}$), here as part of a provider response BTRP($C_{XAB}$). The tentative copy is a copy of a set of privacy sensitive data units at least subject to availability thereof with the second certified party server (B). The tentative copy may include copies of privacy sensitive data units that are not specifically requested by the first certified party server, and it may also include copies for which no authorization is given for making these available with the first certified party server. The certified intermediary server further issues a censored request YSRQ($I_{XAMB}$). Therewith the certified intermediary server requests the at least a second certified server to provide its signature for only the subset of the privacy sensitive data units which it copied in the tentative copy, i.e. the subset that is specifically indicated in the primary request to the extent that authorization for making it available to the first certified party server. Subsequently, the at least a second certified server provides its provider response BSRP($\Gamma_{XAMB}$) including the requested signature ($\Gamma_{XAMB}$), or makes this available to the intermediary server Y in another way to the certified intermediary server. As an optional security step S74, the at least a second certified server may check that the privacy sensitive data for which a signature is requested does not include other data than that what was specified in the primary request. Upon accepting the requested signature by the certified intermediary server the certified intermediary server composes S78 the digitally signed censored copy from a prepared censored copy and the digital signature made available by the at least a second certified party server. Therein the prepared censored copy is provided by the certified intermediary server from the tentative copy, i.e. by selecting from that tentative copy the copied privacy sensitive data units for which it issued the censored request. The step S76 of preparing the censored copy by the certified intermediary server may take place while the at least a second certified party server processes the censored request. Subsequently, the certified intermediary server further makes available to the first certified party server the composed digitally signed censored copy ($C_{XAMB}$,$\Gamma_{XAMB}$) as the digitally signed authorized copy, for example by transmitting a response YCRP($C_{XAMB}$,$\Gamma_{XAMB}$) including the digitally signed authorized copy to the first certified party server.

Figure 10E:
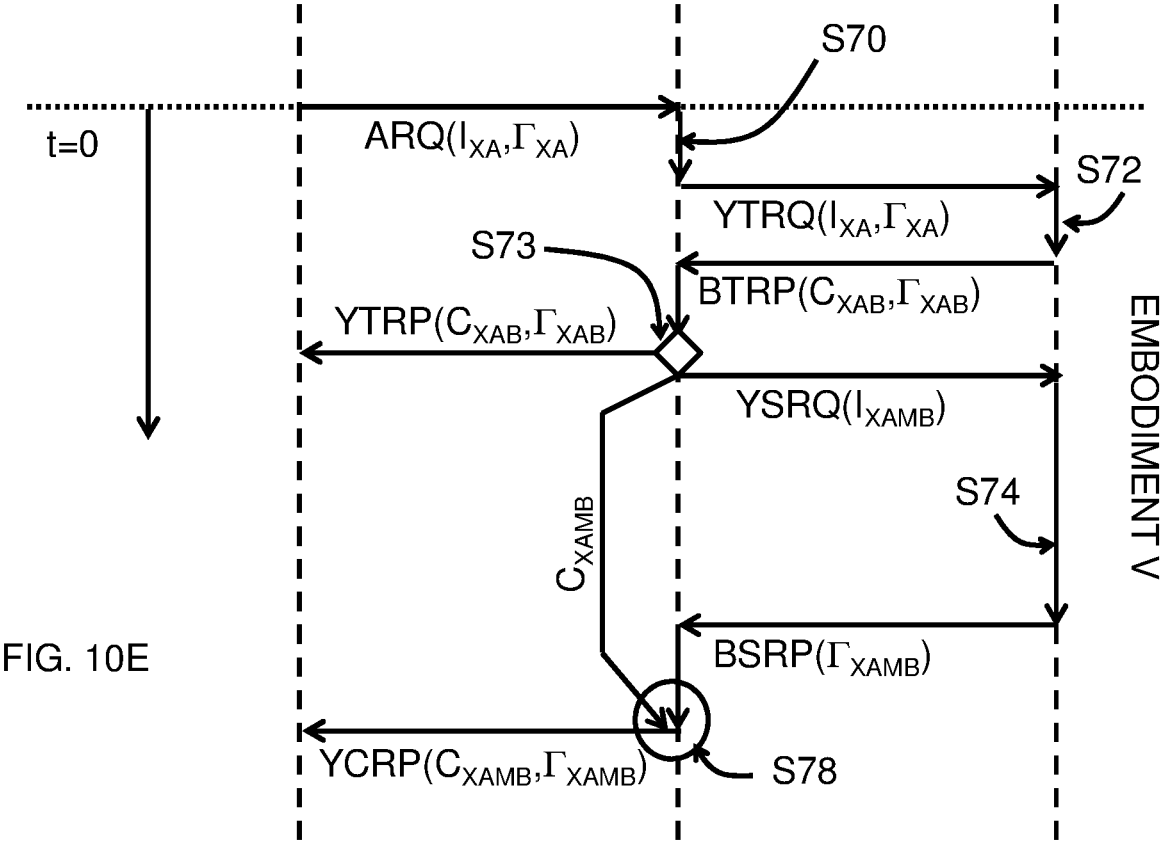

A still further embodiment is shown in FIG. 10E. The embodiment of FIG. 10E substantially corresponds to the embodiment of FIG. 10D. Steps corresponding to those in FIG. 10D are indicated with the same reference. A difference is however that in response to the tentative request, the at least a second certified server provides a digitally signed tentative copy ($C_{XAB}$,$\Gamma_{XAB}$), i.e. in addition to the tentative copy it provides its digital signature associated with the contents in the tentative copy. If the certified intermediary server upon receipt of this digitally signed tentative copy in a verification step S73 determines that it complies with the authorizations provided by the authorizing party, and that it does not include copies of privacy sensitive data units other than requested by the certified first party server, it makes available the digitally signed tentative copy ($C_{XAB}$,$\Gamma_{XAB}$) as the digitally signed authorized copy, for example by transmitting it in a message YTRP($C_{XAB}$,$\Gamma_{XAB}$) to the first certified party server. This is also the case if the at least a digitally signed copy made available by the at least a second certified server is replaced by a digitally signed indication of an empty copy ($C_{\emptyset B}$,$\Gamma_{\emptyset B}$), i.e. an indication $C_{\emptyset B}$ indicating that no copied data is available and a digital signature $\Gamma_{\emptyset B}$ of the at least a second party, associated with that indication. If compliance is affirmed the remainder of the procedure including issuing the censored request can be skipped. Otherwise, the procedure continues in the same way as described with reference to FIG. 10D.

It is noted that data processing facilities used in a certified party server or in a certified intermediary server may be implemented in various ways. E.g. these facilities may be provided as a suitably programmed general purpose processor, as a dedicated hardware, i.e. specifically designed for performing the specified data processing tasks, or as partly programmable processors having some dedicated hardware and being programmable in a restricted application range. Also combinations of such elements may be used.

It will be understood that the certified intermediary server may in fact be a combination of a plurality of servers. Thus it may comprise a first server and a second server, wherein the first server acts through the second server, such as a proxy server or relay server. I.e. this may be the case for example if the first certified party server and the certified intermediary server are incorporated in a first private network and the second certified party server is part of a second private network. The certified intermediary server may communicate via a proxy server in the second network. The further server may have an additional controlling function, or may simply operate as a relay station.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

The invention claimed is:

1. A method for exchanging privacy sensitive data on a public network between a first certified party server associated with a first party and at least a second certified party server associated with at least a second party therewith using a certified intermediary server for controlling said exchanging subject to authorizations imposed by an authorizing party, the method comprising:
    issuing by the first certified party server a primary request requesting the certified intermediary server to execute a query procedure with the at least a second certified party server, the primary request at least including a primary request indication specifying a set of privacy sensitive data units for which the first certified party server requests a copy and a digital signature of the first party, associated with the primary request indication, the primary request indication and the digital signature associated therewith forming a digitally signed primary request;
    executing a query procedure wherein:
        the certified intermediary server makes available the digitally signed primary request to the at least a second certified party server, and
        the at least a second certified party server:
            inspects the digital signature to verify authenticity of the primary request,
            subject at least to a confirmation of said authenticity, makes available for the first certified party server copies of a privacy sensitive data units including at least a copy of a censored subset of privacy sensitive data units, the censored subset comprising the privacy sensitive data units as specified by the primary request indication, and subject at least to said authorizations and subject to availability thereof with the at least a second certified party server, further makes available a digital signature of the at least a second party, associated with said censored subset; and making available to the first certified party server a digitally signed authorized copy, the digitally signed authorized copy including the copy of said censored subset and the digital signature of the at least a second party, associated with said censored subset, wherein the certified intermediary server uses an authorization control table including a set of indications indicating for each pair of certified party servers associated in the system the subset of privacy sensitive data units for which authorizing party has authorized certified party server to provide a copy to certified party server.

2. The method according to claim 1, wherein the authorizations indicate the subset of privacy sensitive data units for which the authorizing party has given an explicit authorization to transfer a copy from a certified party server to another certified party server.

3. The method according to claim 1, wherein the authorizations indicate the subset of privacy sensitive data units for which the authorizing party has not prohibited to transfer a copy from a certified party server to another certified party server.

4. The method according to claim 1, wherein the authorizations include restrictions on providing knowledge of said certified party servers about these authorizations.

5. The method according to claim 1, wherein the authorizations include restrictions as to which extent the at least a second certified party server may be informed about the existence of a request for information about privacy sensitive data units.

6. The method according to claim 1, wherein the authorizations are provided as one or more general authorization rules.

7. The method according to claim 6, wherein the authorizing party has authorized transmission of any indications about availability of privacy sensitive data or have authorized transmission of any copies of privacy sensitive data from the at least a second certified party server to the first certified party server.

8. The method according to claim 6, wherein the one or more general authorization rules at least specify that authorization depends on a quality certificate for an institution associated with a certified party server.

9. The method according to claim 1, wherein the authorizations are specific.

10. The method according to claim 9, wherein the authorizing party has authorized transmission of any indications about availability of specific privacy sensitive data units or have authorized transmission of copies of specific privacy sensitive data units from the at least a second certified party server B to the first certified party server A.

11. The method according to claim 1, further comprising providing said authorizations to the certified intermediary server by the authorizing party or by a deputy authorized by the authorizing party.

12. The method according to claim 11, wherein the certified intermediary server stores the authorizations provided by the authorizing party in a secure storage space forming part of that server or controlled by that server, and prior to controlling said exchanging, accesses the authorizations in said secure storage space to subject said exchanging to said authorizations.

13. The method according to claim 11, wherein the certified intermediary server, requests the authorizing party to provide said authorizations on a case to case basis.

14. The method according to claim 1, wherein an authorization for providing a copy of a subset of privacy sensitive data units from a certified party server to another certified party server B differs from an authorization for providing a copy of a subset of privacy sensitive data units from said certified party server to said certified party server.

15. The method according to claim 1, wherein the at least a second certified party server upon determining that a subset of privacy sensitive data units for which it is authorized to and capable of making available a copy for the first certified party server, is an empty set, and/or wherein the at least a second certified party server if it is not authorized: makes available as the digitally signed authorized copy an indication indicating that said subset is empty and a digital signature of the at least a second party, associated with said indication and/or wherein the digitally signed authorized copy is also made available to the authorizing party.

16. The method according to claim 1, wherein said query procedure includes:

as part of said controlling, determining by the certified intermediary server for which subset of privacy sensitive data units indicated in the primary request indication authorization is given by the authorizing party for making available a copy by the at least a second certified party server to the first certified party server, said subset being indicated by a censored request indication, and requesting by the certified intermediary server the at least a second certified party server with a censored request including the censored request indication, to make available a copy of said subset of privacy sensitive data units indicated by the censored request, the censored request further at least including the digitally signed primary request received from the first certified party server, in response to the censored request making available by the at least a second certified party server for the first certified party server a digitally signed censored copy, including a copy of privacy sensitive data units as indicated by the censored request indication, at least subject to their availability with the at least a second certified party server and a digital signature of the at least a second party, associated with said copy, the digitally signed censored copy being the digitally signed authorized copy.

17. The method according to claim 1, wherein said query procedure includes:

issuing a tentative request by the certified intermediary server to be processed by the at least a second certified party server, the tentative request including at least the digitally signed primary request, wherein the at least a second certified party server in response to said tentative request makes available to the certified intermediary server a tentative copy, being a copy of a set of privacy sensitive data units of said authorizing party at least subject to availability thereof with the at least a second certified party server, as part of said controlling, verifying by the certified intermediary server which authorizations are given by the authorizing party to make available copied privacy sensitive data units in the tentative copy to first certified party server, at least if said verifying indicates that the tentative copy includes copies of privacy sensitive data units for which authorization is not given, issuing by the certified intermediary server a censored request, the censored request at least including an authorization indication specifying an authorized subset of privacy sensitive data units, said authorized subset being the collection of privacy sensitive data units according to the primary request indication subject to at least the authorizations provided by the authorizing party, in response to said censored request, making available by the at least a second certified party server at least a digital signature of the at least a second party, associated with the authorized subset of privacy sensitive data units, making available for the first certified party server a digitally signed censored copy, including a censored copy, and the digital signature of the at least a second party associated with the authorized subset, the censored copy being a copy of said authorized subset, the digitally signed censored copy being the authorized copy.

18. The method according to claim 17, wherein the tentative copy, is restricted to a copy of the set of privacy sensitive data units available with the at least a second certified party server that are indicated in the primary request indication.

19. The method according to claim 17, wherein the at least a second certified party server, in response to said censored request, makes available for said first certified party server the digitally signed censored copy, comprising a censored copy, being a copy of the authorized subset of privacy sensitive data units, in addition to its digital signature.

20. The method according to claim 19, wherein the at least a second certified party server in response to said tentative request further makes available the tentative copy as part of a digitally signed tentative copy, the digitally signed tentative copy further including the digital signature of the at least a second certified party associated with the privacy sensitive data units for which copies are provided in said tentative copy, and wherein upon a positive result of said verifying the certified intermediary server makes available to the first certified party server a digitally signed tentative copy, including said tentative copy, and said digital signature, the digitally signed tentative copy being the digitally signed authorized copy.

21. The method according to claim 19, wherein the certified intermediary server also upon a positive result of said verifying issues a censored request, wherein the authorization indication in the censored request indicates the privacy sensitive data for which the at least a second certified party provided the tentative copy.

22. The method according to claim 17, wherein said censored copy is prepared by the certified intermediary server from said tentative copy, and wherein the certified intermediary server further composes the digitally signed censored copy from said prepared censored copy and the digital signature made available by the at least a second certified party server in response to the censored request, and wherein the certified intermediary server further makes available to the first certified party server the composed digitally signed censored copy as the digitally signed authorized copy.

23. The method according to claim 17, wherein the at least a second certified party server, in response to said censored request, provides its digital signature only subject to confirmation by the at least a second certified party server that the authorization indication does not specify privacy sensitive data units other than those specified by the primary request indication.

24. The method according to claim 1, wherein said query procedure includes:

issuing by the certified intermediary server an availability indication request that includes at least the digitally signed primary request, wherein the at least a second certified party server indicates the certified intermediary server which privacy sensitive data units related to the authorizing party are available with the at least a second certified party server by an availability indication, as part of said controlling, verifying by the certified intermediary server for which subset of the requested privacy sensitive data units indicated as available with the at least a second certified party server authorization is given to make a copy thereof available by the at least a second certified party server to the first certified party server, by the certified intermediary server issuing a censored request, requesting the at least a second certified party server to make available a copy of said subset of privacy sensitive data units indicated by the censored request, making available by the at least a second certified party server to the first certified party server, a digitally signed censored copy including a censored copy of the privacy sensitive data units indicated in the censored request, the digitally signed censored copy further including a digital signature of the at least a second party, associated with the censored copy, the digitally signed censored copy being the digitally signed authorized copy.

25. The method according to claim 24, wherein the availability indication, indicates only availability of privacy sensitive data units as indicated in the primary request.

26. The method according to claim 16, wherein the at least a second certified party server makes available the censored copy, directly to the first certified party server.

27. The method according to claim 16, wherein the at least a second certified party server makes available the censored copy, to the first certified party server via the certified intermediary server.

28. The method according to claim 16, wherein the at least a second certified party server selectively makes available a first portion of the censored copy directly to the first certified party server and a second portion of the censored copy to the first certified party server via the certified intermediary server.

29. The method according to claim 28, wherein as part of said controlling, the certified intermediary server further verifies if said digitally signed censored copy indeed complies with the authorizations provided by the authorizing party, and only makes available the digitally signed censored copy to the first certified party server if it confirms compliance.

30. The method according to claim 1, wherein the certified intermediary server, upon receipt of the primary request, selects one or more of a plurality of second certified party servers as the at least a second certified party server and performs said query procedure with said one or more selected second certified party servers.

31. The method according to claim 30, wherein the certified intermediary server makes said selection upon inspection of an availability table that indicates which of the plurality of second certified party servers can at least partly comply with the primary request.

32. The method according to claim 28, wherein the certified intermediary server executes said query procedure with a plurality of second certified party servers, including the at least one second certified party server, and wherein said plurality of second certified party servers make available respective digitally signed authorized copies to the certified intermediary server, and wherein the certified intermediary server combines the respective digitally signed authorized copies in a single response to the first certified party server.

33. The method according to claim 1, wherein the authorizations that are provided by the authorizing party include an end time indication indicating an end time, wherein said controlling exchanging by said certified intermediary server includes determining a current point in time, and disabling said exchanging if said current point in time is later than said end time.

34. The method according to claim 1, wherein the authorizations that are provided by the authorizing party include a begin time indication indicating a begin time, wherein said controlling exchanging by said certified intermediary server includes determining a current point in time, and disabling said exchanging if said current point in time is earlier than said begin time.

35. A secured system for exchange of privacy sensitive data on a public network, the system including a first certified party server comprising a hardware programmed processor and associated with a first party, at least a second certified party server comprising a hardware programmed processor and associated with at least a second party, and a certified intermediary server comprising a hardware programmed processor and configured for controlling exchange of said privacy sensitive data between the first and the at least a second certified party server subject to authorizations imposed by an authorizing party, the first certified party server being configured to issue a primary request requesting the certified intermediary server to execute a query procedure with the at least a second certified party server, the primary request at least including a primary request indication specifying a first set of privacy sensitive data units for which a copy is requested, and a digital signature of the first party, associated with the primary request indication, the primary request indication and the digital signature associated therewith forming a digitally signed primary request, the at least a second certified party server and the certified intermediary server being configured to execute the query procedure in which:

the certified intermediary server is configured to make available to the at least a second certified party server the digitally signed primary request, and the at least a second certified party server is configured to:

verify the digital signature included in the digitally signed primary request to determine authenticity of the digitally signed primary request, subject to confirming said authenticity the at least a second certified party server, is further configured to make available for the first certified party server copies of privacy sensitive data units including at least a copy of a censored subset of privacy sensitive data units, the censored subset comprising the privacy sensitive data units as specified by the primary request indication subject at least to said authorizations, and subject to availability thereof with the at least a second certified party server, to make further available for the first certified party server a digital signature of the at least a second party, associated with the censored subset; and the secured system being configured to make available to the first certified party server as a digitally signed authorized copy, the copy of said censored subset and the digital signature of the at least a second party, associated with said censored subset, wherein the certified intermediary server uses an authorization control table including a set of indications indicating for each pair of certified party servers associated in the system the subset of privacy sensitive data units for which authorizing party has authorized certified party server to provide a copy to certified party server.

36. A certified intermediary server comprising a hardware programmed processor and configured to control an exchange of privacy sensitive data between a first certified party server and at least a second certified party server in accordance with authorizations provided by an authorizing party, the certified intermediary server comprising a communication facility, an authenticity verification facility, and an exchange authorization controller, the communication facility being configured to accept a digitally signed primary request from the first certified party server in a secure manner using a public network, the digitally signed primary request indication at least including a primary request indication specifying a set of privacy sensitive data units for which the first certified party server requests a copy and a digital signature of the first party, associated with the primary request indication, which communication facility is further configured to execute a query procedure with the at least a second certified party server in a secure manner using the public network, which query procedure includes at least:

making available the digitally signed primary request by the certified intermediary server to the at least a second certified party server, and requesting the at least a second certified party server to make available copies of a privacy sensitive data units including at least a copy of a censored subset of privacy sensitive data units, the censored subset comprising the privacy sensitive data units as specified by the primary request indication subject at least to said authorizations and subject to availability thereof with the at least a second certified party server, and to further make available a digital signature of the at least a second party, associated with said censored subset; and wherein the authenticity verification facility is configured to provide a verified identity indication of the first and the at least a second certified party, and wherein the exchange authorization controller is configured to control exchange of information of privacy sensitive data in accordance with said authorizations, based on the verified identity indication, which communication facility is further configured to make available to the first certified party server, or to request the at least a second certified party server to make available to the first certified party server a digitally signed authorized copy comprising the copy of said censored subset and the digital signature of the at least a second party, associated with said censored subset, wherein the certified intermediary server uses an authorization control table including a set of indications indicating for each pair of certified party servers associated in the system the subset of privacy sensitive data units for which authorizing party has authorized certified party server to provide a copy to certified party server.

37. A certified party server comprising a hardware programmed processor and configured to operate as a second certified party server in a system further comprising a first certified party server comprising a hardware programmed processor and a certified intermediary server comprising a hardware programmed processor and configured to control exchange of privacy sensitive data according to authorizations given by an authorizing party, the configured certified party server comprising a communication facility, an authenticating facility, an authenticity verification facility, a privacy sensitive data management unit, and a privacy sensitive data storage facility, the communication facility being configured to engage in a query procedure with the certified intermediary server and therein at least accepting from the certified intermediary server a digitally signed primary request originating from the first certified party server, the digitally signed primary request indication at least including a primary request indication specifying a set of privacy sensitive data units for which the first certified party server requests a copy and a digital signature of the first party, associated with the primary request indication, wherein the authenticity verification facility is configured to confirm or deny that the digitally signed primary request is authentic, wherein subject to confirming authenticity by the authenticity verification facility, the configured certified party server is configured to proceed in said query procedure in that:

(a) the privacy sensitive data management unit is configured to create a provider copy including at least a censored copy, being a copy of a censored subset of privacy sensitive data units, the censored subset comprising the privacy sensitive data units as specified by the primary request indication subject at least to said authorizations and subject to availability thereof with the at least a second certified party server;

(b) the authenticating facility is configured to create a second party digital signature, being the digital signature of a second party controlling the configured certified party server, associated with said censored subset;

(c) the communication facility is configured to make available for the first certified party server said censored copy and said second party digital signature, said censored copy and said second party digital signature being a digitally signed authorized copy, wherein the certified intermediary server uses an authorization control table including a set of indications indicating for each pair of certified party servers associated in the system the subset of privacy sensitive data units for which authorizing party has authorized certified party server to provide a copy to certified party server.

* * * * *